US007517654B2

(12) United States Patent
Min et al.

(10) Patent No.: US 7,517,654 B2
(45) Date of Patent: Apr. 14, 2009

(54) PEPTIDE AND A DERIVATIVE THEREOF PROMOTING CELL ADHESION AND SPREADING

(75) Inventors: Byung-Moo Min, Seoul (KR); Jin-Man Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 463 days.

(21) Appl. No.: 10/555,590

(22) PCT Filed: Jul. 8, 2005

(86) PCT No.: PCT/KR2005/002205

§ 371 (c)(1),
(2), (4) Date: Nov. 4, 2005

(87) PCT Pub. No.: WO2006/025646

PCT Pub. Date: Mar. 9, 2006

(65) Prior Publication Data

US 2008/0096792 A1    Apr. 24, 2008

(30) Foreign Application Priority Data

Sep. 2, 2004    (KR) .................. 10-2004-0069941

(51) Int. Cl.
*G01N 33/53* (2006.01)
*A61K 38/04* (2006.01)
*A61K 39/00* (2006.01)
*A61K 38/00* (2006.01)

(52) U.S. Cl. .................. 435/7.1; 530/327; 530/328; 530/329; 424/185.1; 514/14; 514/15; 514/16

(58) Field of Classification Search ............ None
See application file for complete search history.

(56) References Cited

U.S. PATENT DOCUMENTS 6,933,580 B2 * 8/2005 Chen et al. ............ 257/413
2003/0104999 A1    6/2003 Iozzo

OTHER PUBLICATIONS

Goldfinger et al. Spatial regulation and activity modulation of plasmin by high affinity binding to the G domain of the alpha 3 subunit of laminin-5. J Biol Chem. Nov. 10, 2000;275(45):34887-93.*
Aberdam, Daniel, et al., Herlitz's junctional epidermolysis bullosa is linked to mutation in the gene (LAMC2) for the gamma 2 subunit of . . . , Nature Genetics, 1994, pp. 299-304, vol. 6.
Aumailley, Monique, et al., Laminins of the dermo-epidermal junction, Matrix Biology, 1999, pp. 19-28, vol. 18, No. 1.
Baker, S. E., et al., Laminin-5 and hemidesmosomes: role of the alpha 3 chain subunit in hemidemosome stability and assembly, Journal of Cell Sciences, 1996, pp. 2509-2520, vol. 109, No. 10.
Burgeson, R. E., et al., A new nomenclature for the laminins, Matrix Biology, 1994, pp. 209-211, vol. 14, No. 3.
Carter, William G., et al., Epiligrin, a new cell adhesion ligand for integrin a3b1 in epithelial basement membranes, Cell, 1991, pp. 599-610, vol. 65.
Clark, E. A. and Brugge, J. S., Integrins and signal transduction pathways: the road taken, Science, 1995, pp. 233-239, vol. 268, No. 5208.
Colognato, H., et al., Form and function: the laminin family of heterotrimers, Dev. Dyn., 2000, pp. 213-234, vol. 218, No. 2.
Dipersio, C. M., et al., alpha 3A beta 1 integrin localizes to focal contacts in response to diverse extracellular matrix proteins, Journal of Cell Science, 1995, pp. 2321-2336, vol. 108, No. 6.
Ekblom, Marja, et al., Laminin isoforms and epithelial development, Annals of the New York Academy of Sciences, 1998, pp. 194-211, vol. 857, Publisher: New York Academy of Sciences, Published in: New York, NY.
Giancotti, F. G. and Ruoslahti, E., Integrin signaling, Science, 1999, pp. 1028-1032, vol. 285, No. 5430.
Guan, J. L., Role of focal adhesion kinase in integrin signaling, Int. Journal of Biochem. Cell Biol., 1997, pp. 1085-1096, vol. 29, No. 8-9.
Hirosaki, Tomomi, Structural requirement of carboxyl-terminal globular domains of laminin alpha 3 chain for promotion of rapid cell . . . , Journal of Biol. Chem., 2000, pp. 22495-22502, vol. 275, No. 29.
Howe, Alan, et al., Integrin signaling and cell growth control, Current Opinion in Cell Biology, 1998, pp. 220-231, vol. 10, No. 2.
Kariya, Y., et al., Differential regulation of cellular adhesion and migration by recombinant laminin-5 forms with partial deletion or . . . , Journal of Cell Biochem., 2003, pp. 506-520, vol. 88, No. 3.
Korge, B. P., et al., The molecular basis for inherited bullous diseases, Journal of Molecular Medicine, 1996, pp. 59-70, vol. 74, No. 2.
Lampe, Paul D., et al., Cellular interaction of integrin alpha 3 beta 1 with laminin 5 promotes gap junctional communication, Journal of Cell Biol., 1998, pp. 1735-1747, vol. 143, No. 6.
Marinkovich, M. P., et al., The anchoring filament protein kalinin is synthesized and secreted as a high molecular weight precursor, Journal of Biol. Chem., 1992, pp. 17900-17906, vol. 267, No. 25.

(Continued)

*Primary Examiner*—Maher M Haddad
(74) *Attorney, Agent, or Firm*—Kelly Reynolds; Steven J. Hultquist; Intellectual Property/Technology Law

(57) ABSTRACT

The present invention relates to a peptide promoting cell adhesion and spreading, fragments, and derivatives thereof, more particularly, integrin-α3β1-dependent peptide in human laminin-5 α3 chain LG3 domain, mediating integrin α3β1 binding and cell adhesion and spreading, fragments and derivatives thereof. The inventive peptide, fragments and derivatives thereof can be used effectively for research on cell adhesion activity, wound care, tissue regeneration, inhibition of cancer metastasis etc. mediated by various extracellular matrix protein including laminin.

7 Claims, 18 Drawing Sheets

OTHER PUBLICATIONS

Mercurio, Arthur M., et al., The alpha 6 beta 4 integrin and epithilial cell migration, Current Opinion in Cell Biology, Oct. 1, 2001, pp. 541-545, vol. 13, No. 5.

Min, Byung-Moo, et al., Terminal differentiation of normal human oral keratinocytes is associated with enhanced cellular TGF-beta and . . . , Experimental Cell Research, 1999, pp. 377-385, vol. 249, No. 2.

Miner, Jeffrey H., et al., The laminin alpha chains: expression, developmental transitions, and chromosomol locations of alpha 1-5 . . . , Journal of Cell Biology, 1997, pp. 685-701, vol. 137, No. 3.

Mizushima, H., et al., Identification of integrin-dependent and -independent cell adhesion domains in COOH-terminal globular region . . . , Cell Growth & Differentiation, 1997, pp. 979-987, vol. 8, No. 9.

Niessen, C. M., et al., The a6b4 integrin is a receptor for both laminin and kalinin, Experimental Cell Research, 1994, pp. 360-367, vol. 211, No. 2.

Okazaki, Ikuko, et al., Identification of biologically active sequences in the laminin alpha 4 chain G domain, Journal of Biol. Chem., 2002, pp. 37070-37078, vol. 277, No. 40.

Park, N. H., et al., Immortalization of normal human oral ketatinocytes with type 16 human papillomavirus, Carcinogenesis, 1991, pp. 1627-1631, vol. 12, No. 9.

Rodeck, U., et al., EGF-R dependent regulation of keratinocyte survival, Journal of Cell Science, 1997, pp. 113-121, vol. 110, No. 2.

Rousselle, P., et al., Kalinin: an epithelium-specific basement membrane adhesion molecule that is a component of anchoring filaments, Journal of Cell Biology, 1991, pp. 567-576, vol. 114.

Rousselle, P., et al., Kalinin is more efficient than laminin in promoting adhesion of primary keratinocytes and some other epithelial cells . . . , Journal of Cell Biology, 1994, pp. 205-214, vol. 125.

Schlaepfer, D. D., et al., Integrin-mediated signal transduction linked to Ras pathway to GRB2 binding to focal adhesion kinase, Nature, 1994, pp. 786-791, vol. 372, No. 6508.

Schoenwaelder, Simone M., et al., Evidence for a calpeptin-sensitive protein-tyrosine phosphatase upstream of the small GTPase rho, Journal of Biol. Chem., 1999, pp. 14359-14367, vol. 274, No. 20.

Schwartz, M. A., et al., Integrins: emerging paradigms of signal transduction, Annual Rev. Cell Dev. Biol., 1995, pp. 549-599, vol. 11.

Shang, Meiling, et al., The LG3 module of laminin-5 harbors a binding site for integrin alph 3 beta 1 that promotes cell adhesion, spreading, . . . , Journal of Biol. Chem., 2001, pp. 33045-33053, vol. 276, No. 35.

Talts, J. F., et al., Structural analysis and proteolytic processing of recombinant G domain of mouse laminin alpha2 chain, FEBS Lett., 1998, pp. 71-76, vol. 426, No. 2.

Timpl, Rupert, Macromolecular organization of basement membranes, Current Opinion in Cell Biology, 1996, pp. 618-624, vol. 8, No. 5.

Timpl, Rupert, et al., Structure and function of laminin LG modules, Matrix Biology, 2000, pp. 309-317, vol. 19, No. 4.

Tsubota, Y., et al., Isolation and activity of proteolytic fragment of laminin-5 alpha 3 chain, Biochem. Biophys. Res Commun., 2000, pp. 614-620, vol. 278, No. 3.

Utani, Atsushi, et al., A unique sequence of the laminin alpha 3 G domain binds to heparin and promotes cell adhesion through syndecan-2 and -4, Journal of Biol. Chem., 2001, pp. 28779-28788, vol. 276, No. 31.

Zhang, Ken, et al., Laminin 5 deposition promotes keratinocyte motility, Experimental Cell Research, 1996, pp. 309-322, vol. 227, No. 2.

* cited by examiner

| Peptide | Sequence |
|---|---|
| P4 | PPFLMLLKGSTR |
| P4 D-I | PPFLMLLKGST |
| P4 D-II | PPFLMLLKGS |
| P4 D-III | PPFLMLLKG |
| P4 D-IV | PPFLMLLK |
| P4 D-V | PPFLMLL |
| P4 D-N1 | PFLMLLKGSTR |
| P4 D-N2 | FLMLLKGSTR |
| P4 D-N3 | LMLLKGSTR |
| P4 D-N4 | MLLKGSTR |
| P4 D-N5 | LLKGSTR |
| P4 D-N6 | LKGSTR |

FIG. 7A
| Peptide | Sequence |
|---|---|
| P4 | PPFLMLLKGSTR |
| P4-S1 | PPFLMLLAGSTR |
| P4-S2 | PPFLMLLKGSTA |
| P4-S3 | PPFLMLLAGSTA |
FIG. 7B
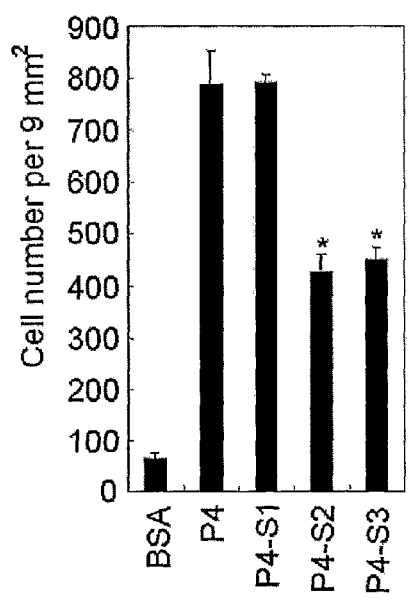
FIG. 7C
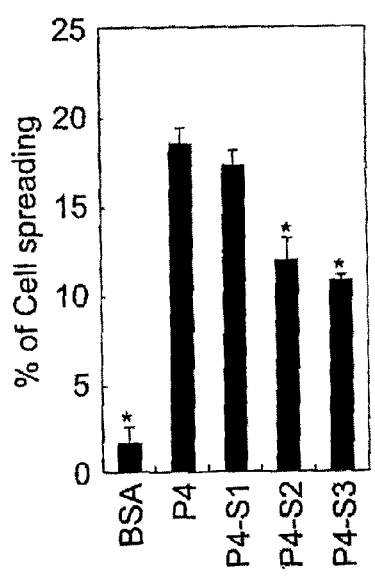

ns a C-termi-
PEPTIDE AND A DERIVATIVE THEREOF PROMOTING CELL ADHESION AND SPREADING

CROSS-REFERENCE TO RELATED APPLICATIONS

This application is filed under the provisions of 35 U.S.C. §371 and claims the priority of International Patent Application No. PCT/KR2005/002205 filed Jul. 8, 2005, which in turn claims the priority of Korean Patent Application No. 10-2004-0069941 filed Sep. 2, 2004.

TECHNICAL FIELD

The present invention relates to integrin-α3β1-dependent peptide in the LG3 domain of human laminin-5 α3 chain, which mediates cell adhesion and spreading, fragments and derivatives thereof.

BACKGROUND ART

Laminins are a family of extracellular matrix proteins localized primarily in the basement membranes which regulate various cellular functions such as adhesion, motility, growth, differentiation, wound healing, and tumor invasion through an interaction with specific integrins or other receptors on the cell surface (Timpl, R., Curr. Opin. Cell Biol., 8: 618, 1996; Howe, A. et al, Curr. Opin. Cell Biol., 10:220, 1998; Colognato, H. and Yurchenco, P. D., Dev. Dyn., 218: 213, 2000). Laminins consist of three different subunits (α, β and γ chains) which form the cross-shaped structure linked by disulfide bonds (Ekblom, M. et al., Ann. N. Y Acad. Sci., 857:194, 1998). Thus far, 5α, 3β and 3γ chains have been identified, at least 15 isoforms (laminin 1-15) are formed by various combinations of these subunits (Colognato, H. and Yurchenco, P. D., Dev. Dyn., 218:213, 2000; Burgeson, R. E. et al., Matrix Biol., 14:209, 1994; Miner, J. H. et al., J. Cell Biol., 137:685, 1997). Among these laminin isoforms, laminin-5, an isoform consisting of α3, β3, and γ2 chains, has a unique structure and biological activity. Laminin-5 was originally identified as a keratinocyte-derived matrix protein (Carter, W. G. et al., Cell, 65:599, 1991), but, unlike other isoforms, it lacks some domains found in the N-terminal regions of the three subunits (Aumailley, M. and Rousselle, P., Matrix Biol., 18:19, 1999). The laminin-5 precursor (460 kDa) is processed in keratinocytes. This precursor is secreted, followed by the proteolytic conversion of the α3 chain (200 kDa) and the γ2 chain (155 kDa) to 165 and 105 kDa, respectively (Marinkovich, M. P. et al., J. Biol. Chem., 267:17900, 1992; Rousselle, P. et al., J. Cell Biol., 114:567, 1991).

Laminin-5 regulates the stable adhesion of the epithelium to the underlying connective tissue (Marinkovich, M. P. et al., J. Biol. Chem., 267:17900, 1992; Rousselle, P. et al., J. Cell Biol., 114:567, 1991; Niessen, C. M. et al., Exp. Cell. Res., 211:360, 1994), and influences the cell's behavior by interacting with cell surface receptors, such as integrins α3β1 and α6β4 (Carter, W. G. et al., Cell, 65:599, 1991; Rousselle, P. et al., J. Cell Biol., 114:567, 1991; Niessen, C. M. et al., Exp. Cell. Res., 211:360, 1994; Rousselle, P. and Aumailley, M., J. Cell Biol., 125:205, 1994). Among the integrins expressed in normal human keratinocytes, integrin α3β1 is involved in the formation of focal adhesions, which are associated with actin-containing stress fibers and mediation of keratinocyte motility (DiPersio, C. M. et al., J. Cell Sci., 108:2321, 1995; Zhang, K. and Kramer, R. H., Exp. Cell. Res., 227:309, 1996). Integrin α6β4 forms the hemidesmosome structure of epithelial cells, mediates adhesion, migration, and wound healing of epithelial cells, and is involved in the invasion of carcinoma cells (Niessen, C. M. et al., Exp. Cell. Res., 211:360, 1994; Mercurio, A. M. et al, Curr. Opin. Cell Biol., 13:541, 2001). Mutations in laminin-5 or integrin α6β4 cause a Herlitz-type junctional epidermolysis bullosa, which is characterized by a splitting of the epidermal/dermal junctions (Aberdam, D. et al., Nat. Genet., 6:299, 1994; Korge, B. P. and Krieg, T., J. Mol. Med., 74:59, 1996).

Besides laminin-5, the laminin α3 chain is found in laminin-6(α3β1γ1), laminin-7(α3β2γ1) and laminin-13 (α3β2γ3), however the laminin β3 and γ2 chains are found only in laminin-5. The laminin α3 chain contains a C-terminal globular domain that consists of five globular modules LG1-LG5, each approximately 200 amino acid residues in length (Talts, J. F. et al., FEBS Lett., 426:71, 1998; Timple, R. et al., Matrix Biol., 19:309, 2000). Mapping studies using various laminin isoforms have mapped the localization of the integrin-dependent cell adhesion site to the globular domain of laminin α chains (Baker, S. E. et al., J. Cell Sci., 109:2509, 1996; Hirosaki, T. et al., J. Biol. Chem., 275:22495, 2000). The C-terminal LG3 domain in the α3 chain is essential for the unique activity of laminin-5. Recombinant LG3 (rLG3) domain in rats and recombinant laminin-5 proteins serially lacking the LG domains in humans promote cell adhesion and migration by interacting with integrin α3β1 (Hirosaki, T. et al., J. Biol. Chem., 275:22495, 2000; Shang, M. et al., J. Biol. Chem., 276:33045, 2000). Studies on the rLG proteins of the human laminin α3 chain have shown that the LG2 domain contains an integrin α3β1-binding site, while the LG4 and LG5 domains weakly interact with the heparin sulfate proteoglycans (Mizushima, H. et al., Cell Growth Differ., 8:979, 1997). In addition, while the LG4-LG5 fragment of the laminin α3 chain, itself does not exhibit activity, it stimulates cell migration in the presence of the mature laminin-5, which suggests a regulatory role in cell migration (Tsubota, Y. et al., Biochem. Biophys. Res. Commun., 278:614, 2000). However, the direct demonstration of integrin-dependent cell adhesion in the human laminin α3 chain LG3 domain has not been reproduced using rLG domain fragments, possibly due to difficulties in expressing the soluble LG proteins.

Meanwhile, it has been recognized that the primary adhesion site of laminins is located in the C-terminal LG domain region of laminin a chains. Various LG domains of the laminin α chain have been shown to mediate cell adhesion and migration and bind to heparin, α-dystroglycan, syndecans, and integrins (Howe, A. et al., Curr. Opin. Cell Biol., 10:220, 1998). Although it has been demonstrated that the LG3 domain of the human laminin-5 α3 chain is essential for the promotion of cell adhesion and motility by laminin-5 (Hirosaki, T. et al., J. Biol. Chem., 275:22495, 2000), there has not been any further report on the active sites for the biological functions and integrin binding in the LG3 domain.

Accordingly, to clarify the functions of the LG domains of the human laminin-5 α3 chain and to further determine biologically active core sequences, the present inventors prepared the recombinant human laminin-5 α3 chain LG domains expressed in the form of monomeric, soluble fusion proteins and synthetic peptides within the LG3 domain of the laminin-5 α3 chain, and examined their cell adhesion and spreading activities. As a result, the present inventors confirmed that human laminin-5 α3 LG3 domain promoted cell adhesion and spreading activities by acting as a ligand for integrin α3β1, and a motif PPFLMLLKGSTR (1312-1323 residues) of the SEQ ID NO:1 within the LG3 domain, fragments and derivatives thereof are important for cell adhesion and spreading activities as an active site for integrin α3β1 binding, and show excellent cell adhesion activity with Beschitin W microfiber thus can be used in wound care or tissue regeneration, thereby completing the present invention.

DISCLOSURE OF THE INVENTION

It is a main object of the present invention to identify an active domain in human laminin-5 α3 chain mediating cell adhesion and spreading and integrin binding, and to provide a peptide which functions as an essential motif promoting cell adhesion and spreading activities by specifically binding with integrin in the domain, fragments, derivatives thereof and use thereof.

To achieve the above object, the present invention provides a peptide having amino acid sequence of SEQ ID NO: 1, fragments or derivatives thereof, which mediates cell adhesion and spreading and functions as an essential motif for cell adhesion and spreading.

In addition, the present invention provides a peptide (rLG-His$_6$) having amino acid sequence of SEQ ID NO: 13, which promotes cell adhesion and spreading or derivatives thereof.

The above and other features and embodiments of the present invention will be more fully apparent from the following detailed description and appended claims.

BRIEF DESCRIPTION OF DRAWINGS

FIG. 7A shows amino acid sequences of Ala-substituted peptides (P4-S1(SEQ ID NO: 29), P4-S2 (SEQ ID NO: 30), and P4-S-3 (SEQ ID NO: 31)) of peptide P4.

FIGS. 7B and 7C are graphs showing cell adhesion activities and spreading activities of the Ala-substituted peptides.

DETAILED DESCRIPTION OF THE INVENTION

In the present invention, five individually expressed recombinant LG proteins (rLG1 to rLG5) are prepared to identify active domains in human laminin-5 α3 chain mediating cell adhesion and spreading and integrin binding.

Figure 1A:
FIG. 1A illustrates schematic diagram of the laminin-5 α3 chain domains and their recombinant proteins
Figure 1B:
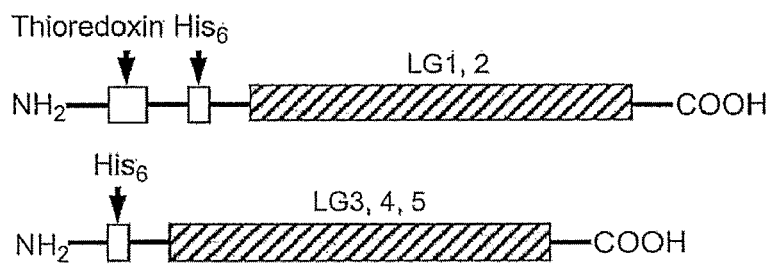
FIG 1B illustrates schematic diagram of recombinant LG proteins (rLG1-rLG5) in the laminin-5 α3 chain domains, expressed in the form of His6-tagged fusion proteins.
Figure 1C:
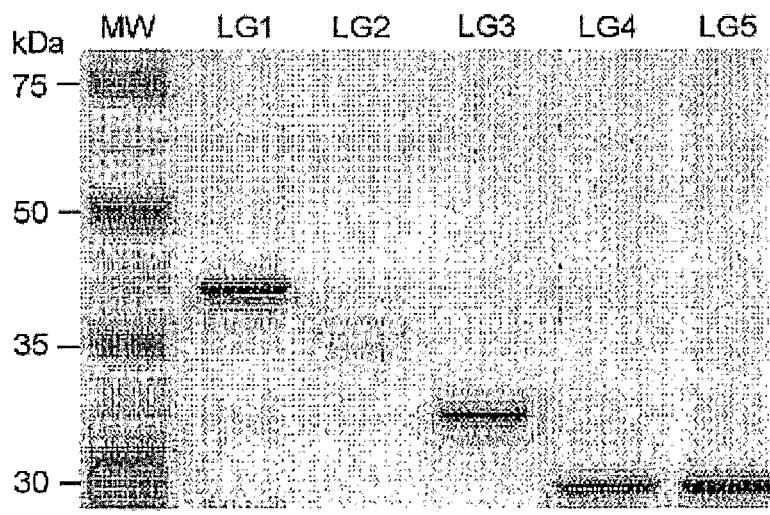
FIG. 1C is a result of purifying recombinant LG proteins in human laminin-5 α3 chain domain by SDS-PAGE.

Among the rLG proteins prepared according to the present invention, rLG1 contains 782-978 residues in amino acid sequence of human laminin α3 chain of SEQ ID NO: 2, and rLG2, rLG3, rLG4 and rLG5 contain 959-1148 residues, 1128-1364 residues, 1352-1555 residues and 1522-1713 residues, respectively. In addition, the rLG proteins are expressed in the form of fusion protein bound with six histidine tags in the C-terminal as a detecting probe to facilitate their purification (FIGS. 1A and 1B).

cDNA fragments containing DNA sequence encoding each LG domain and DNA sequence encoding each detecting probe were prepared, and then an expression vector inserted with the cDNA fragments was prepared. The expression vector was transformed into E. coli to obtain a transformant and recombinant proteins are expressed in the obtained transformant, followed by purifying the rLG1-rLG5 from expressed proteins using detecting probe (FIG. 1C).

As a result of cell adhesion and spreading activity examination of rLG1-rLG5 isolated/purified from the E.coli transformant, only rLG3 protein exhibited cell adhesion activity among the five rLG proteins (FIGS. 2A-2C), and the adhesion of HOK-16B cell on rLG3 was dose-dependent, with the maximum adhesion occurring at a 25 μg/ml coating concentration. In the rLG3-coated plates, 47% of the HOK-16B cells displayed a spreading morphology; that is, they adopted a flattened, polygonal shape, with filopodia- and lamellipodia-like extensions (FIG. 2D). These results suggest that the rLG3 protein displays functional properties similar to laminin-5, its parent molecule, because it supports cell adhesion and spreading. In addition, LG3 domain-mediated cell adhesion and spreading were mediated by integrin α3β1, this suggests that integrin α3β1 is the primary receptor for laminin in human keratinocytes and laminin is an important ligand for keratinocyte adhesion and spreading activities.

Figures 3, 4A:
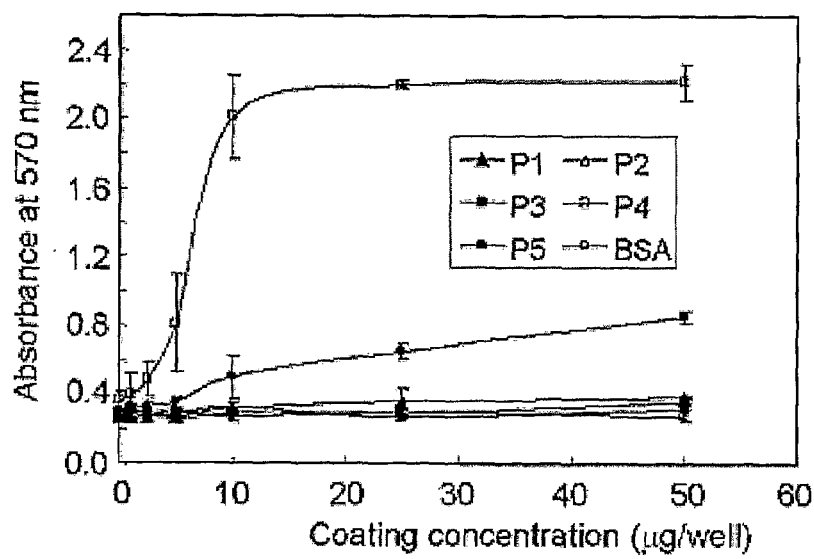
FIG. 3 shows a comparison between amino acid sequences of part of the laminin α3 LG3 domains of humans (SEQ ID NO: 14), rats (SEQ ID NO: 15), mice (SEQ ID NO: 16) and dogs (SEQ ID NO: 17) and the arrows indicate the locations of the synthetic peptides.
FIG. 4A shows a measurement of cell adhesion activities of synthetic peptides (P1-P5) derived from human laminin-5 α3 LG3 domain according to the concentration changes.
Figure 4B:
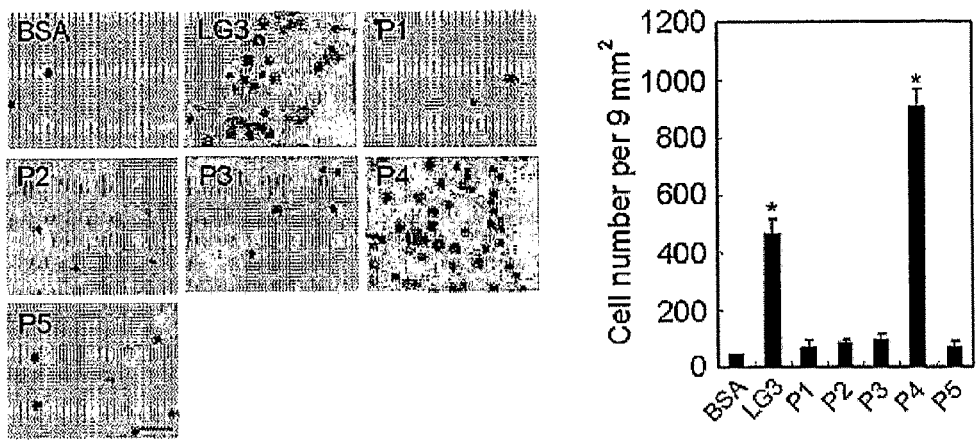
FIG. 4B shows a measurement of cell adhesion activities of the synthetic peptides and the number of adhered cells in HOK-16B cells.
Figure 4C:
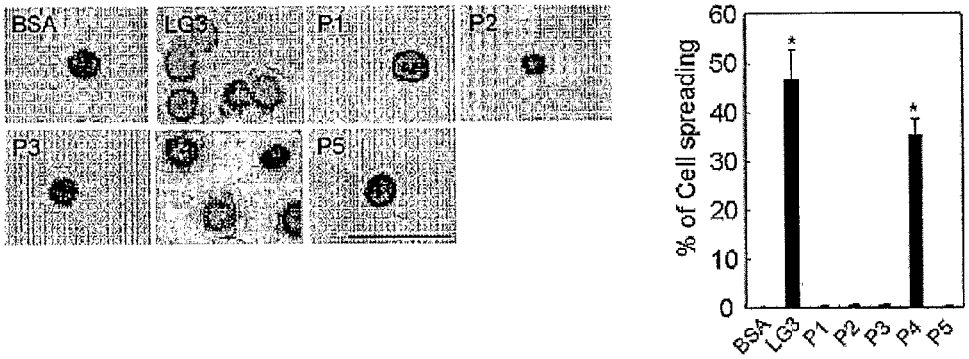
FIG. 4C shows a measurement of cell spreading activities of the synthetic peptides in HOK-16B cells.

To identify the essential amino acid residues conferring cell adhesion activity of the laminin α3 chain LG3 domain, five overlapping 12-mer peptides (P1-P5) covering amino acid residues 1293-1332 derived from the LG3 domain were synthesized (FIG. 3). Among the synthesized peptides as the above, P1 contains 1293-1304 residues in the amino acid sequence of SEQ ID NO: 2, P2 contains the amino acid sequence corresponding to 1297-1308 residues, P3 contains the amino acid sequence corresponding to 1305-1316 residues, P4 contains the amino acid sequence corresponding to 1312-1323 residues, and P5 contains the amino acid sequence corresponding to 1321-1332 residues. As a result of examination for cell adhesion and spreading activities of the synthesized peptides, peptide P4 having PPFLMLLKGSTR sequence of SEQ ID NO: 1 showed strong dose-dependent cell adhesion and spreading activities similar to rLG3 (FIGS. 4A-4C).

Figure 4D:
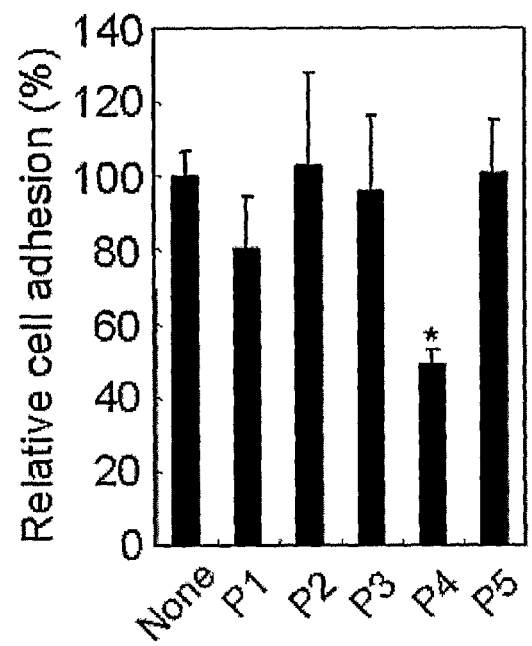
FIG. 4D is a graph showing results of examining the effect of preincubation of HOK-16B cells with the synthetic peptides on inhibition of HOK-16B cell adhesion to recombinant LG3 protein in human laminin-5 α3 chain.

The present inventors found that the cell spreading activity of peptide P4 is similar to that of rLG3, and examined the ability of peptide P4 to compete for cell adhesion activity to LG3 domain. As a result, the peptide P4 inhibited cell adhesion to rLG3 by approximately 51%, but none of the other peptides showed reduced adhesion activity in HOK-16B cells preincubated for 30 min with 100 μg/ml of the peptides (FIG. 4D). These suggest that the peptide P4 sequence functions as a cell binding site in the intact laminin-5 α3 chain LG domain.

In addition, the inventive rLG3 protein and peptide P4 showing cell adhesion and spreading are specifically inhibited by antibodies to the α3 and β1 subunits (FIGS. 5B and 5C), this suggests that integrin α3β1 is a specific functional receptor for both rLG3 and peptide P4 in HOK-16B cells.

Figures 6A, 6B:
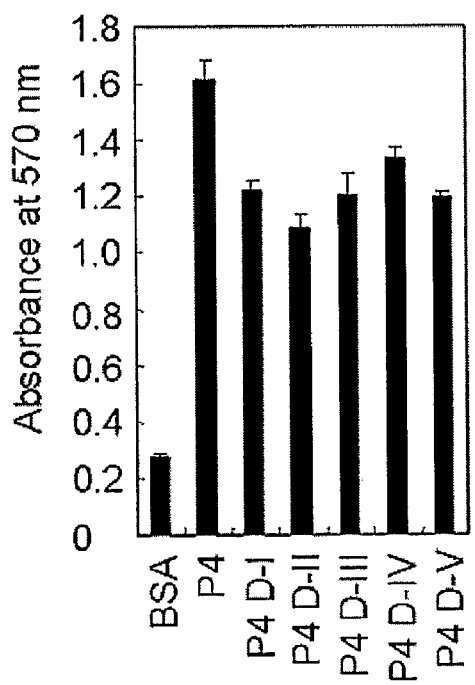
FIG. 6A shows amino acid sequences of C-terminal truncated peptides (P4 D-1(SEQ ID NO: 18), P4 D-II (SEQ ID NO: 19), P4 D-III (SEQ ID NO: 20), P4 D-IV (SEQ ID NO: 21), and P4 D-5(SEQ ID NO: 22)) and N-terminal truncated peptides (P4 D-N1(SEQ ID NO: 23), P4 D-N2(SEQ ID NO: 24), P4 D-N3 (SEQ ID NO: 25), P4 D-N4 (SEQ ID NO: 26), P4 D-N5 (SEQ ID NO: 27), and P4 D-N6 (SEQ ID NO: 28)) of synthetic peptide P4 derived from human laminin-5 α3 chain LG3 domain.
FIG. 6B is a graph showing cell adhesion activities of control BSA (bovine serum albumine) and the C-terminal truncated peptides (P4 D-I , P4 D-III and P4 D-V).
Figure 6C:
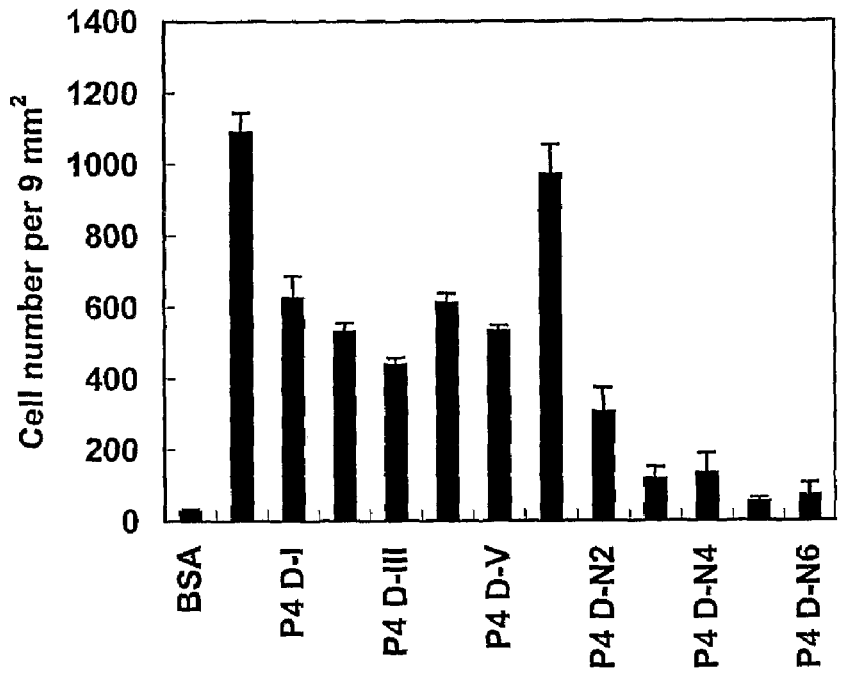
FIG. 6C is a graph showing the number of cells adhered to control BSA (bovine serum albumine), the C-terminal truncated peptides (P4 D-I , P4 D-III and P4 D-V) and the N-terminal truncated peptides (P4 D-N2, P4 D-N4 and P4 D-N6).
Figure 6D:
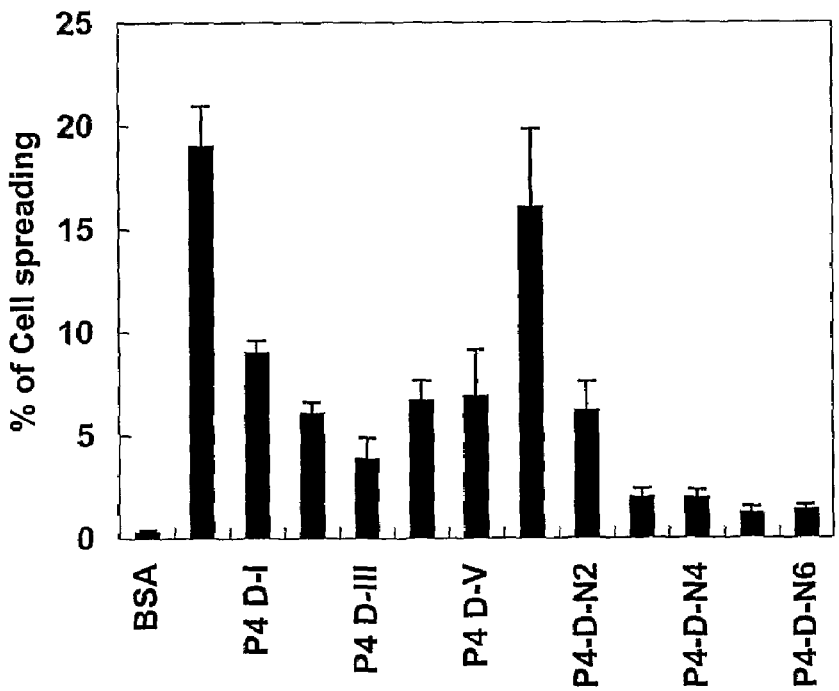
FIG. 6D is a graph showing cell spreading activities of control BSA (bovine serum albumine), the C-terminal truncated peptides (P4 D-I , P4 D-III and P4 D-V) and the N-terminal truncated peptides (P4 D-N2, P4 D-N4 and P4 D-N6)

To determine the biologically active core sequences in peptide P4 having SEQ ID NO: 1, which are identified to promote strong cell adhesion and spreading activities and to bind with integrin α3β1, five synthetic peptides (P4 D-I to D-V), which are C-terminal truncated peptides from the peptide P4, and six synthetic peptides (P4 D-N1, to P4 D-N6), which are N-terminal truncated peptides from the peptide P4, were prepared (FIG. 6A). As a result of examination for cell adhesion and spreading activities of C-terminal truncated peptides and N-terminal truncated peptides, peptide P4 D-I, which has a deletion of the C-terminal Arg residue in peptide P4, showed significantly lower cell adhesion and spreading activities than the peptide P4 control (FIGS. 6B-6D), and peptide P4 D-N2, which has deletions of the N-terminal two Pro residues in peptide P4, showed significantly lower cell adhesion and spreading activities than the peptide P4 control (FIGS. 6C-6D)

Thus, it was demonstrated that both the deletion of the C-terminal Arg residue and the deletions of the N-terminal two Pro residues in peptide P4 reduced the cell adhesion and spreading activities significantly. However, peptide P4 D-N1, which has a deletion of one of the N-terminal two Pro residues in peptide P4, did not show a great change in cell adhesion and spreading activities. This shows that peptide P4 fragments, which has a deletion of one of the N-terminal two Pro residues in peptide P4, is also useful as a peptide promoting cell adhesion and spreading.

Accordingly, to verify the role of two basic amino acid residues, Arg and Lys, in the peptide P4 sequence of SEQ ID NO: 1, synthetic peptides were prepared by substituting Ala for both/each $Lys^{1319}$ and $Arg^{1323}$ in the peptide P4 sequence (P4-S1 and P4-S3, FIG. 7A), and the inventors examined their cell adhesion and spreading activities. As a result, the cell adhesion and spreading were significantly inhibited by peptides P4-S2, in which Ala had been substituted for Arg, and P4-S3, in which Ala had been substituted for Lys and Arg, compared to the peptide P4 control. However, these activities were unaffected by peptide P4-S1 where Ala had been substituted for Lys (FIGS. 7B and 7C). Therefore, the basic residue Arg in peptide P4 is important for cell adhesion activity. These results suggest that the PPFLMLLKGSTR sequence (residues 1312-1323) within the laminin-5 α3 chain LG3 domain is an active motif responsible for cell adhesion and spreading and for integrin α3β1-binding.

Figure 8A:
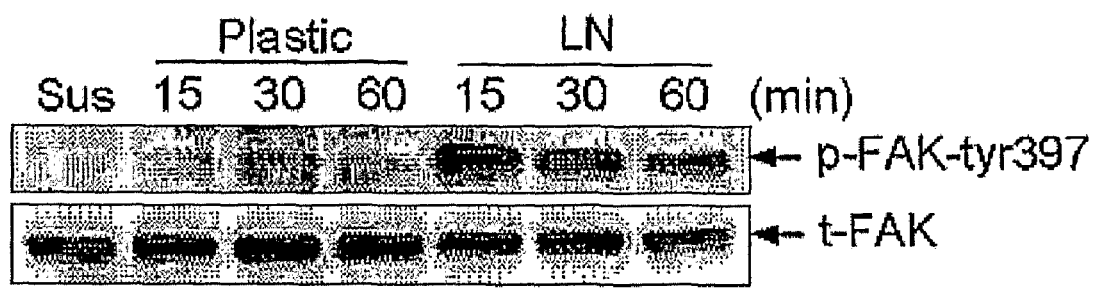
FIG. 8A shows the effect of laminin on FAK phosphorylation at tyrosine-397 by immunoblot analysis.
Figure 8B:
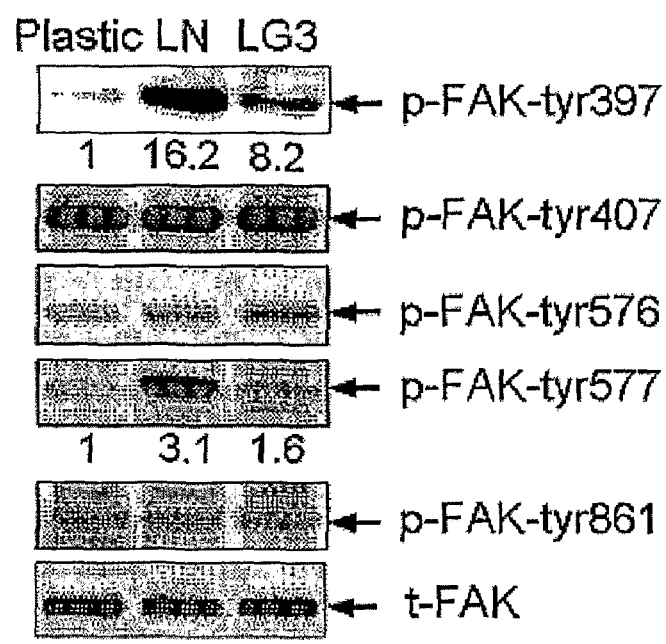
FIG. 8B shows the effect of human laminin-5 α3 recombinant LG3 protein on FAK phosphorylation at various tyrosine sites by immunoblot analysis.

Meanwhile, to examine the signaling pathways mediated by either the LG3 domain or peptide P4, the phosphorylation of FAK was examined in HOK-16B cells plated on either rLG3 or peptide P4. As a result, the extent of FAK phosphorylation in HOK-16B cells on laminin-coated plate was notably higher than that in HOK-16B cells which were either plated on laminin-uncoated plate or kept in suspension (FIG. 8A). In addition, the extent of FAK phosphorylation at Tyr-397, -407, -576, -577, and -861 in HOK-16B cells cultured on plates coated with laminin, rLG3, or peptides P1-P5 was investigated. In consequence, the extent of FAK phosphorylation at Tyr-397 in HOK-16B cells cultured on the laminin-coated or rLG3 protein-coated plates increased 16.2- and 8.2-fold compared with the untreated control (FIG. 8B).

Figure 9A:
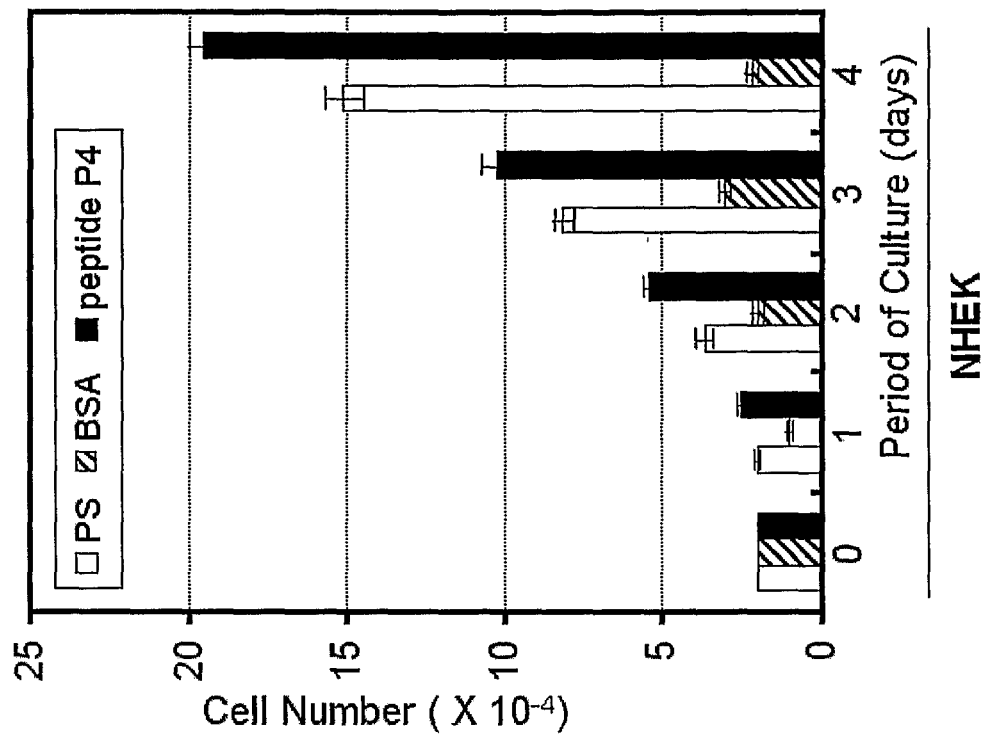
FIG. 9A is a graph showing an increase in the number of NHEKs according to NHEK cell proliferation on 24-well plates coated with polystyrene (PS), BSA (bovine serum albumin) and synthetic peptide P4.
Figure 9B:
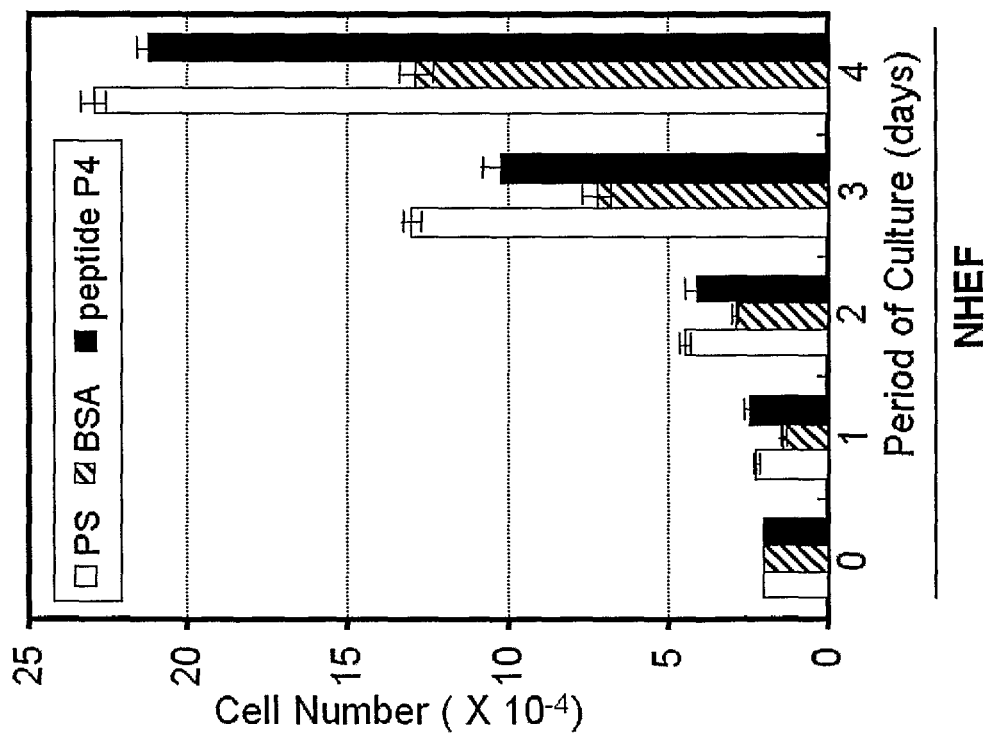
FIG. 9B is a graph showing an increase in the number of NHEFs according to NHEF cell proliferation on 24-well plates coated with polystyrene (PS), BSA (bovine serum albumin) and synthetic peptide P4.
Figure 10A:
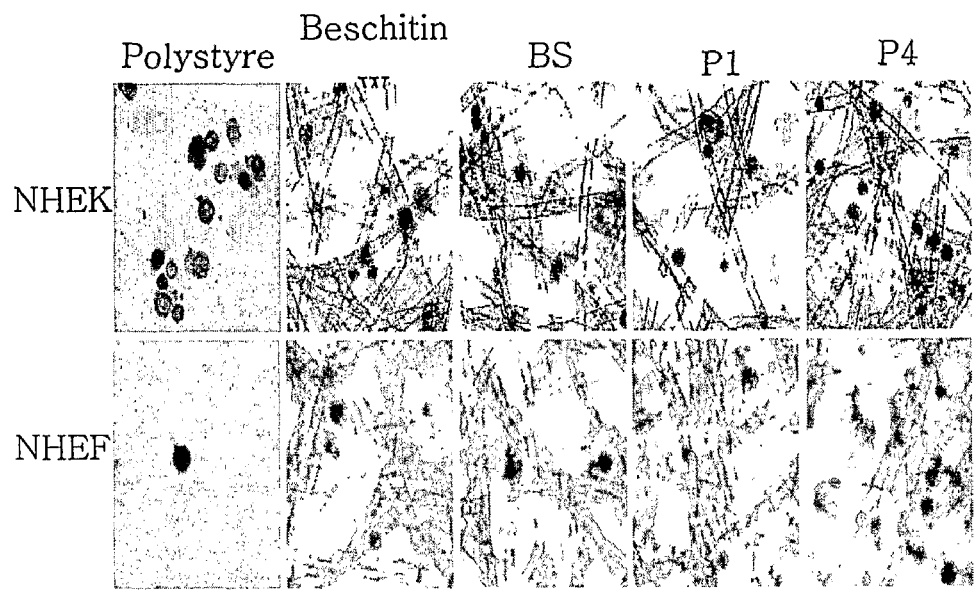
FIGS. 10A-10C show the results of cell adhesion activities, the number of adhered cells and spreading cell rates of NHEK and NHEF as compared with those of other controls, respectively (PS: polystyrene; Beschitin W only: Beschitin W microfiber; BSA: beschitin W microfiber treated with bovine serum albumin; P1: beschitin W microfiber treated with peptide P1 as control; and P4: beschitin W microfiber treated with functional peptide P4).
Figure 10B:
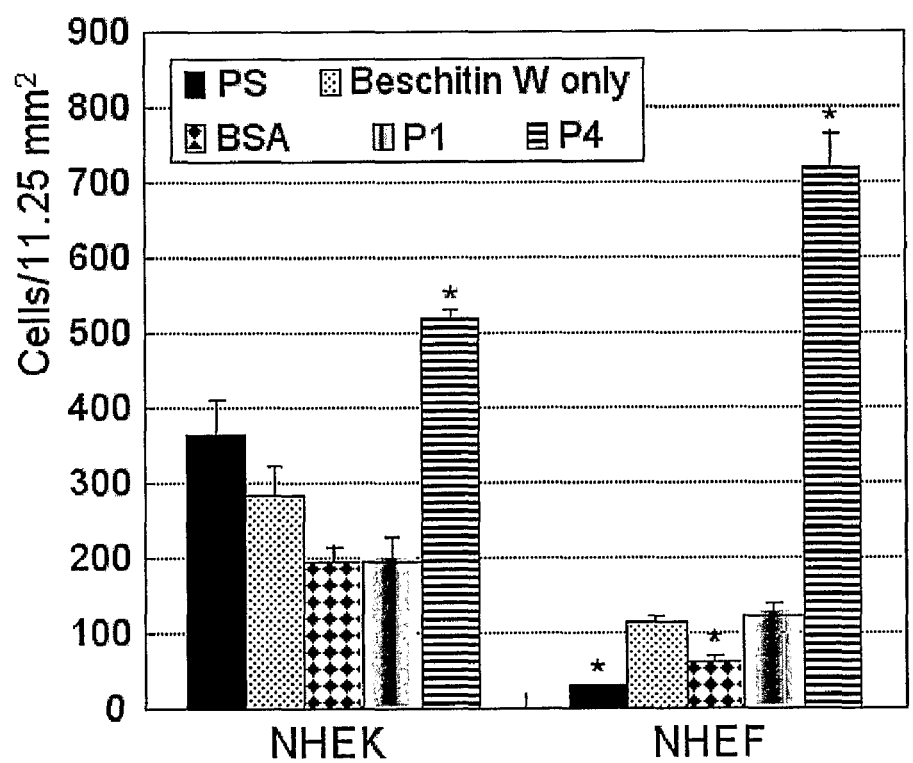
Figure 10C:
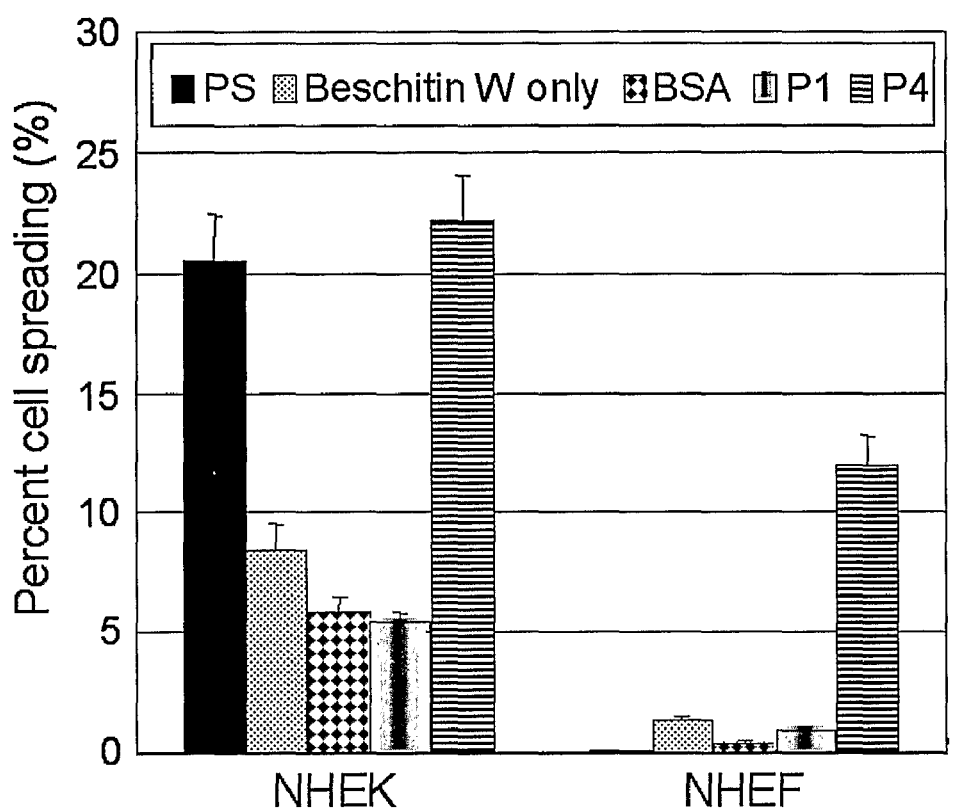

Also, an increase in the number of cells according to cell proliferation of normal human epidermal keratinocytes (NHEK) and normal human epidermal fibroblasts (NHEF) by peptide P4, was excellent especially in NHEK (FIGS. 9A and 9B), as a result of examination for cell adhesion and spreading activities, the numbers of adhered cells and spread cells in beschitin W microfiber coated with P4 peptide were more than those of other controls (FIGS. 10A-10C).

From these results, it was demonstrated that unlike the LG1, LG2, LG4, and LG5 domains of the human laminin-5 α3 chain, the LG3 domain is essential for laminin-5 promotion of cell adhesion and spreading in an integrin α3β1-dependent manner. Furthermore, the PPFLMLLKGSTR sequence (1312-1323 residues of SEQ ID NO: 2) within the human LG3 domain of the laminin-5 α3 chain is an active motif capable of supporting integrin α3β1-dependent cell adhesion and spreading.

Also, the levels of FAK phosphorylation at Tyr-397 and -577 increased as a result of adhesion to rLG3 protein and the PPFLMLLKGSTR sequence of SEQ ID NO: 1, which is the first report demonstrating that the PPFLMLLKGSTR peptide of SEQ ID NO: 1 within the LG3 domain is a novel motif that is capable of supporting integrin α3β1-dependent cell adhesion and spreading.

Thus, human laminin-5 α3 recombinant LG3 domain and a peptide of SEQ ID NO: 1, fragments or derivatives thereof according to the present invention can be a substitute for laminin-5 for researches on cell adhesion activity, wound care, tissue regeneration, inhibition of cancer metastasis, tissue engineering and other therapeutical applications.

Accordingly, the present invention provides pharmaceutical composition for wound care, burn treatment, tissue regeneration and inhibition of cancer metastasis, which contains a peptide having an amino acid sequence of SEQ ID NO: 1 in human laminin-5 α3 recombinant LG3 domain, fragments or derivatives thereof as an effective component.

In the present invention, the derivatives have conserved Arg at 12th site or Pro at 1st or 2nd site.

In the present invention, the derivatives are P4-S1, in which the 8th Lys of SEQ ID NO: 1 is replaced by Ala, and the fragments are P4 D-N1, in which any one of the first Pro or second Pro is deleted.

In the present invention, 'fragments' are the ones that one or more amino acids are deleted from a peptide having effective activity, which have the same activity as said peptide or similar activity to said peptide.

In the present invention, 'derivatives' are the ones that one or more amino acids are substituted in a peptide having effective activity, which have the same activity as said peptide or similar activity to said peptide.

The effective component of inventive pharmaceutical composition can be administered parenterally when clinically administered, and is used in the form of general pharmaceutical preparations. That is, the inventive peptide, fragments or derivatives thereof can be administered by various parenteral formulations. In the case of pharmaceutical preparation, they are prepared using generally used diluents, such as fillers, extenders, binders, wetting agents, disintegrants and surfactants, or excipients. The pharmaceutical preparation for parenteral administration includes sterilized water, non-water-soluble solvent, suspension, emulsifier, freeze-drying agent. Vegetable oils, such as propyleneglycol, polyethyleneglycol, olive oil and ethylolate can be used as the non-water-soluble solvent and suspension.

In addition, the peptide, fragments or derivatives thereof can be used by mixing with carrier, such as physiological salt solution or organic solvent, which is allowed to be used as drugs. To increase stability or absorption of peptides, carbohydrates such as glucose, sucrose, or dextran, antioxidants, such as ascorbic acid, or glutathione, chelating agents, low molecular proteins or other stabilizers can be used as drugs.

In the pharmaceutical composition of the present invention, total effective dose can be administered to patients with single dose in the form of bolus or by infusion for relatively short period, and also can be administered with multiple dose for a long period of time by fractionated treatment protocol. The peptide concentration for effective dose is determined by consideration of various factors such as, pharmaceutical administration pathway, treatment frequency, as well as, the age and health condition of patient. Thus, those skilled in the art will be able to determine a proper effective dose of the peptide according to specific use as pharmaceutical composition of the peptide.

The present invention, also, provides wound covering materials and scaffold for tissue engineering including a peptide having amino acid sequence of SEQ ID NO: 1 in human laminin-5 α3 recombinant LG3 domain, fragments, or derivatives thereof.

A skin is an important apparatus which has the functions of protecting the body from outer stimulus and inhibiting water loss from the body. When skin has a damage caused by burns or various external wounds, the function of protection gets lost, which causes a disorder and makes it difficult to treat wound because of various side effects and bacteria infection from the outside and also it brings about additional side effects such as, secondary functional disorder or damage. Thus, to care the wound quickly and minimize the various secondary side effects, wound care must be performed using proper covering materials.

The wound covering materials protect wound caused by skin damage and promote regeneration of skin tissue, which is one of the important medical products essential for growing numbers of patients with skin damage. When burns with broad area is treated, damaged tissue is removed from burnt area and the remaining burnt area is covered with temporary burn covering materials prior to ultimate autotransplantation. Temporary burn covering materials should have several functions for treatment. First, they have the function of a shield which prevents infections caused by microorganism invasion from the outside, as well as, loss of water, salt and protein from the inside. Second, they facilitate purification and regeneration of the wound by promoting wound closure. Third, they alleviate pain.

Thus, it would be ideal that the wound covering materials can contribute even to regeneration of damaged skin cell and wound care with these functions.

Scaffolds for tissue engineering according to the present invention include all scaffolds which can be used in tissue engineering field for maintenance, improvements, or restoration of body functions by transplantation of a substitute for living body tissue. These scaffolds for tissue engineering include porous scaffolds prepared by synthetic biodegradable high molecular compound, such as poly amino acid, poly anhydride, polyε-caprolactone, polyorthoester, polyglycollic acid (PGA), polylactic acid (PLA), their co-polymers, such as polylactic-polyglycollic acid (PLGA), and raw biodegradable high molecular compound, such as alginic acid, chitosan, highalginic acid, and collagen. The scaffolds for tissue engineering can include shields, such as porous polylactic acid shield, a regeneration membrane made of chitin or chitosan nanofiber, or film-shaped shield made of chitin or chitosan, but are not limited thereto.

The inventive peptide containing amino acid sequence of SEQ ID NO: 1 in laminin-5 α3 recombinant LG3 domain, fragments, or derivatives thereof have an excellent cell adhesion and spreading activities. Wound covering materials containing the peptide, fragments, or derivatives thereof are expected to have an excellent function. The Beschitin W microfiber coated with the peptide P4 of the present invention, which is a commercially available artificial skin material, proved these functions by showing excellent cell adhesion activity.

EXAMPLES

Hereinafter, the present invention will be described in more detail by the following examples. It is to be understood, however, that these examples are given for illustrative purpose only and are not construed to limit the scope of the present invention.

Experimental Example 1

Cell Culture

The HOK-16B line, human oral keratinocytes immortalized by transfecting cells with the cloned HPV-16 genome (Park, N. H. et al., *Carcinogenesis*, 12:1627, 1991) was maintained in keratinocyte growth medium containing 0.15 mM calcium and a supplementary growth factor bullet kit (KGM; Clonetics). Normal human oral keratinocytes (NHOKs) were prepared and maintained as described elsewhere (Min, B. M. et al., *Exp. Cell. Res.*, 249:377, 1999). In particular, oral keratinocytes were isolated by trypsin treatment from gingival epithelium tissue of healthy applicants (18 to 30 years old) with dental surgery, then they were primarily cultured in KGM. Primary NHOKs showing about 70% confluence were plated with $1\times10^5$ cells per 60 mm petri dish, then were cultured until 80% conflunence. NHOKs with 80% confluence were subcultured and NHOKs with secondary culture were used in the described experiments.

Experimental Example 2

Cell Adhesion and Spreading Activity Assays

The cell adhesion assay was performed according to a method reported by Okazaki et al. (*J. Biol. Chem.*, 277:37070, 2002). In detail, 24-well culture plates (Nunc, Roskilde, Denmark) were coated with various amounts of rLG proteins at 4° C. overnight. The peptides were also coated on plates by drying overnight. The substrate-coated on the plates were blocked by adding 1% heat-inactivated bovine serum albumin (BSA) in PBS for 1 h at 37° C. and washed twice with PBS. The cells in the Experimental Example 1, detached by 0.05% tyrpsin and 0.53 mM EDTA in PBS and resuspended in culture media, were added ($1\times10^5$ cells/500 μl) to each plate and incubated for 1 h at 37° C. After incubation, unattached cells were removed by rinsing twice with PBS. The attached cells were fixed with 10% formalin in PBS for 15 min, rinsed twice with PBS, and stained with 0.5% crystal violet for 1 h. The plates were gently rinsed with DDW three times and lysed with 2% SDS for 5 min. Absorbance was measured at 570 nm in a Bio-Rad Model 550 microplate reader (BioRad).

To identify spreading cells, attached cells were fixed with 10% formalin in PBS for 15 min, rinsed twice with PBS, and stained with 0.005% crystal violet for 1 h. The plates were then gently rinsed with DDW. To ensure a representative count, each plate was divided into quarters, two fields per quarter were photographed using an Olympus BX51 microscope at 100× magnification. Cells that had adopted a flattened, polygonal shape, with filopodia-and lamellipodia-like extensions were considered to be spreading cells. In contrast, cells that resisted being washed and remained tethered to the plate surface were considered to be non-spreading cells.

Experimental Example 3

Flow Cytometry

The flow cytometry to examine cell surface integrin expression level were performed with a method of Rodeck et al. (*J. Cell Sci.*, 110:113, 1997). Specifically, HOK-16B cells were isolated by gently treating with PBS containing 0.05% trypsin and 0.53 mM EDTA, and washed. Then, the cells were cultured with anti-integrin mAbs (anti-α2, α3, α5, α6, αv, β1 and β4) for 45 min at 4° C. After being washed, the cells were cultured with FITC-labeled secondary antibody for 45 min at 4° C., and analyzed with FACS (Calibur flow cytometer, Becton-Dickinson, San Jose, Calif.).

Experimental Example 4

Adhesion Activity Inhibition Assay

To identify the receptor of the HOK-16B cells for rLG3 protein and peptide P4, 5 μg/ml of mAbs to different types of integrins or 5 mM EDTA were preincubated individually with HOK-16B cells in 0.5 ml incubation solution ($2\times10^5$ cells/ml) for 30 min at 37° C. The preincubated cells were then transferred onto plates precoated with either 25 μg/ml of rLG3 protein or 10 μg/well of peptide P4 and incubated for 1 h at 37° C. Attached cells were then quantified by the cell adhesion assay described above in the Experimental Example 2, and cell adhesion activity inhibition rate were measured.

Experimental Example 5

FAK Phosphorylation Assay

The FAK phosphorylation assays were performed according to a method of Shang et al. (*J. Biol. Chem.*, 276:33045, 2001). In detail, the HOK-16B cells were trypsinized, washed, and kept in suspension in serum-free KGM with 0.1% BSA for 1 h at 37° C. The 60-mm culture dishes were coated with laminin (5 μg/ml) or rLG3 protein (25 μg/ml) at 4° C. overnight. Peptides (50 μg/60-mm culture dish) were also coated on dishes by drying overnight. For the adherent FAK assay, $1\times10^6$ cells were plated onto uncoated, laminin-coated, rLG3 protein-coated, or various peptide-coated dishes and allowed to attach for 15, 30, or 60 min at 37° C. in an atmosphere of 5% $CO_2$. At the end of the incubation, cells were washed with ice-cold PBS and lysed in RIPA buffer (50 mM Tris [pH 7.4], 150 mM NaCl, 1% Nonidet P-40, 0.5% Na-deoxycholate, 1 mM EDTA, 0.1% SDS, 2 mM $Na_3VO_4$, 1 mM glycerol phosphate, 1 mM PMSF, and protease inhibitor cocktail). Lysates were clarified by centrifugation at 12,000×g for 10 min at 4° C. to isolate cytosolic extracts.

The cytosolic extracts were denatured using SDS sample buffer [50 mM Tris-HCl (pH 6.8), 2% SDS, 10% glycerol, 0.1% bromophenol blue, 100 mM β-mercaptoethanol] and separated on an 8% SDS-polyacrylamide gel. Electrophoretic transfer of SDS-PAGE gel separated with protein to a nitrocellulose membrane was followed by immnoblotting with polyclonal anti-FAK antibodies to determine the total FAK level or immnoblotting with polyclonal anti-FAK [$pY^{397}$], [$pY^{407}$], [$pY^{576}$], [$pY^{577}$] or [$pY^{861}$] antibodies to determine the extent of tyrosine phosphorylation. The relative fold induction of FAK phosphorylation, defined as an increase in FAK phosphorylation of a sample relative to its corresponding background level (i.e., cells plated on plastic) was determined as follows: First, the densimomerty intensity of the phosphorylated FAK (p-FAK) and the total FAK (t-FAK) signals from the Western blots were measured with a LAS-1000plus (Fuji photo film, Japan). The ratio of p-FAK to t-FAK (p-FAK/t-FAK) for each sample was then calculated to correct for differences in protein loading. This ratio was normalized to the p-FAK/t-FAK ratio of the negative controls to obtain the relative fold induction of FAK phosphorylation.

Example 1

Expression of rLG Domains of Human Laminin-5 α3 Chain

To identify integrin-binding, adhesive domains of the human laminin-5, the five LG domains of human laminin-5 α3 chain were individually expressed in the form of monomeric, water-soluble recombinant proteins in *E. coli*.

In detail, the human laminin-5 α3 chain cDNA was cloned using a reverse transcriptase-polymerase chain reaction (RT-PCR) with Super-script II Reverse Transcriptase (GibcoBRL, Grand Island, N.Y.) according to the manufacturer's instructions by using mRNA isolated from NHOKs. Five C-terminal LG cDNA fragments (LG1 to LG5) of the laminin-5 α3 chain were amplified by polymerase chain reaction using the cloned laminin-5 α3 chain cDNA as a template and LG1 to LG3 fragments were cloned into the pGEM-T Easy vector (Promega, Madison, Wis.), and LG4 and LG5 fragments were cloned into the pEZ-T vector (RNA, Seoul, Korea). The polymerase chain reaction primers used were as follows: LG1, SEQ ID NO: 3 (sense) and SEQ ID NO: 4 (antisense); LG2, SEQ ID NO: 5 (sense) and SEQ ID NO: 6 (antisense); LG3, SEQ ID NO: 7 (sense) and SEQ ID NO: 8 (antisense); LG4, SEQ ID NO: 9 (sense) and SEQ ID NO: 10 (antisense); LG5, SEQ ID NO: 11 (sense) and SEQ ID NO: 12 (antisense). Nucleotide sequences of all of the plasmid constructs were confirmed by sequence anaylsis. The pGEM-T Easy vector and pEZ-T vector containing LG cDNA fragments were digested with appropriate restriction enzymes. These cDNA fragments were subsequently cloned into either the EcoRI site (LG1) or NcoI-SaI sites (LG2) of the mammalian expression plasmid vector pET-32a (+) (Novagen, Madison, Wis.), or into the EcoRI site (LG3) or NcoI site (LG4 and LG5) of the mammalian expression plasmid vector pRSET (Invitrogen, Carlsbad, Calif.). Correct orientation of the inserts was verified by sequence analysis.

To facilitate the purification of recombinant protein, (His)$_6$-tags were ligated with C-terminal of the recombinant protein in the process. The clones with DNA fragments inserted in correct orientation were selected and mutations or deletions during the process were verified by sequence analysis. *E. coli* strain BL21 transformed with the each expression vector were cultured in LB medium at 37° C. until the OD is 0.5-0.6 at 595 nm, and added with 1 mM isopropyl-β-D-thiogalactopyranoside(Promega) to induce protein expressions of recombinant LG domains. After protein induction for 5 h at 37° C., the cells were harvested by centrifugation at 6000 rpm for 10 min. Cell pellets were stored at −80° C. until use.

For protein purification, the pellets were resuspended in ice-cold lysis buffer (100 mM NaH$_2$PO$_4$, 10 mM Tris-HCl, 8 M urea, pH 8.0) containing 1 mM phenylmethylsulfonyl fluoride (Sigma). Cell lysis was carried out by passing the cell suspension through a 10 ml pipette, with caution to avoid foaming. The clarified cell lysates were applied to a Ni$^{2+}$-nitrilotriacetic acid agarose column (Qiagen, Valencia, Calif.). The column was washed with 10 mM imidazole in lysis buffer, then attached proteins onto the column were eluted using 250 mM imidazole in lysis buffer.

Eluted recombinant proteins were dialyzed sequentially against a solution containing 10 mM Tris-HCl, 100 mM NaH$_2$PO$_4$, 1 mM phenylmethylsulfonyl fluoride, and 3, 2, 1, or 0.5M urea, pH 3.0, finally, the proteins were dialyzed with 1 mM phenylmethylsulfonyl fluoride in PBS (pH 3.0). The dialyzed rLG proteins were concentrated at 0.5 µg/µl with a CentriconYM-10 filter device (Millipore, Bedford, Mass.) and stored at −80° C. until use. The protein concentration was determined using a Bio-Rad protein assay kit (BioRad, Hercules, Calif.).

The corresponding amino acid positions of the recombinant proteins in the entire α3 chain molecule are shown in FIG. 1, the domain structures of the laminin-5 α3 chain (open column) are indicated by IIIa, I/III, and LG1-LG5. The shaded portion represents the signal peptide. The closed bars represent the positions of the recombinant LG proteins prepared according to the present invention, and numbers in parentheses indicate the corresponding amino acid positions of the recombinant LG proteins in the entire α3 chain molecule. Among the prepared rLG proteins, rLG1 contains 782~978 residues, rLG2 contains 959~1148 residues, rLG3 contains 1128~1364 residues, rLG4 contains 1352~1555 residues, rLG5 contains 1522~1713 residues in the amino acid sequence of the human laminin α3 chain of SEQ ID NO: 2.

The prepared recombinant LG proteins in the present invention extended into the neighboring domains by 3 to 25 amino acids to facilitate protein folding and were expressed in the form of N-terminal (His)$_6$-tagged fusion proteins to provide convenient handles for the protein purification and identification assays (FIG. 1C). The rLG1, rLG2, rLG3, rLG4, and rLG5 proteins expressed in the form of monomeric water-soluble fusion protein in *E. coli* according to the present invention, were subjected to SDS-PAGE anaylsis and visualized by Coomassie staining to determine that the molecular weights of the each recombinant proteins were 43,39,32,30, and 29 kDa, respectively. The rLG proteins were purified to near homogeneity with Ni$^{2+}$-nitrilotriacetic acid-agarose under denaturing conditions, as determined by Coomassie staining of a SDS-polyacrylamide gel (FIG. 1C). All five rLG domains showed similar expression levels. On average, approximately 0.5 mg of the purified rLG protein was obtained per 0.5 liters of bacterial culture.

Example 2

Cell Adhesion and Spreading Activities of Human Laminin-5 α3 Chain rLG Proteins

To examine the effect of human laminin-5 laminin-5 α3 recombinant LG proteins prepared in the Example 1 on cell adhesion and spreading, the cell adhesion and spreading activities were analyzed according to the method in the Experimental Example 2.

Figure 2A:
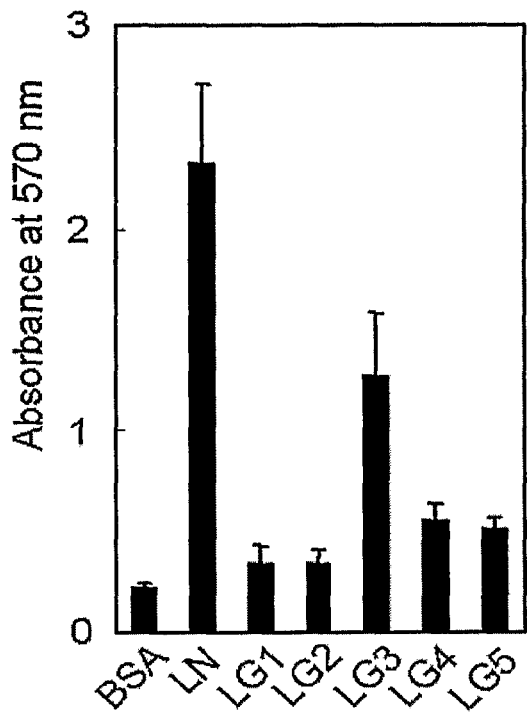
FIG. 2A is a graph showing comparison between cell adhesion activities of recombinant LG proteins in human laminin-5 α3 chain domain and that of human placental laminin (LN).
Figure 2B:
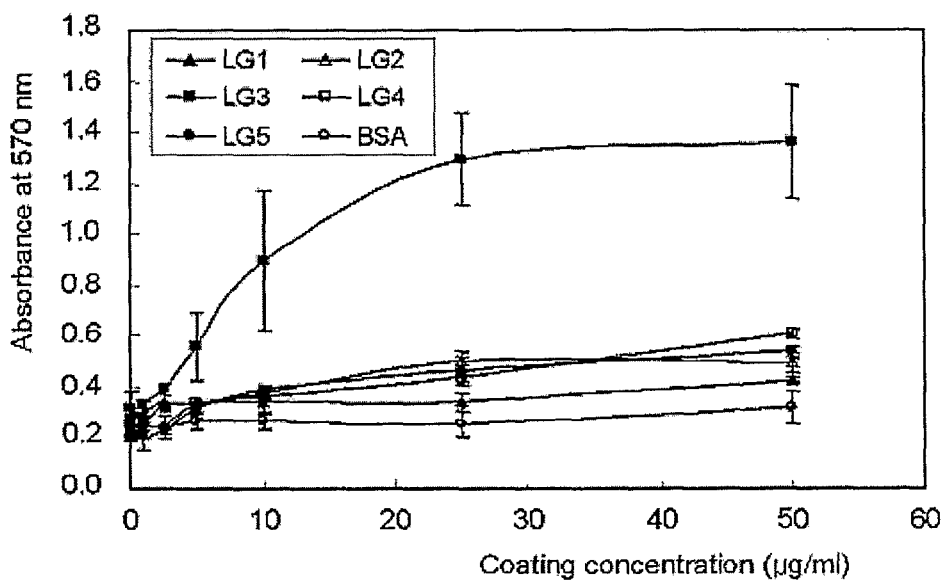
FIG. 2B is a graph showing results of examining the effect of the concentrations of the recombinant LG proteins on cell adhesion activities.
Figure 2C:
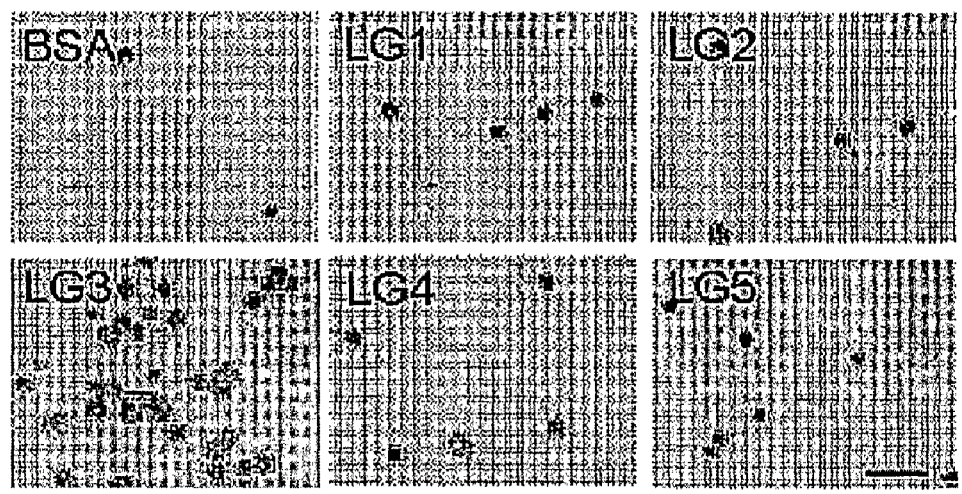
FIG. 2C shows a measurement of cell adhesion activities of the recombinant LG proteins and the number of adhered cells in HOK-16B cells.
Figure 2C:
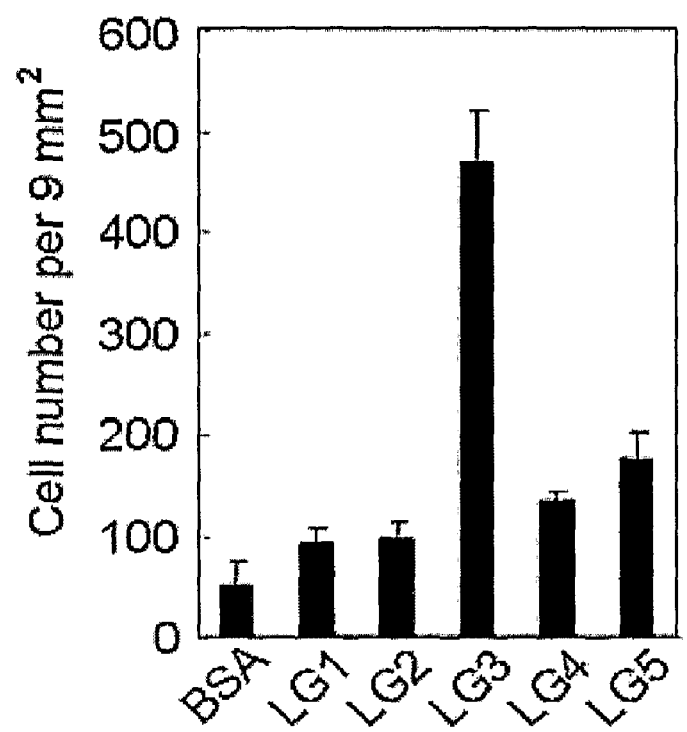
Figure 2D:
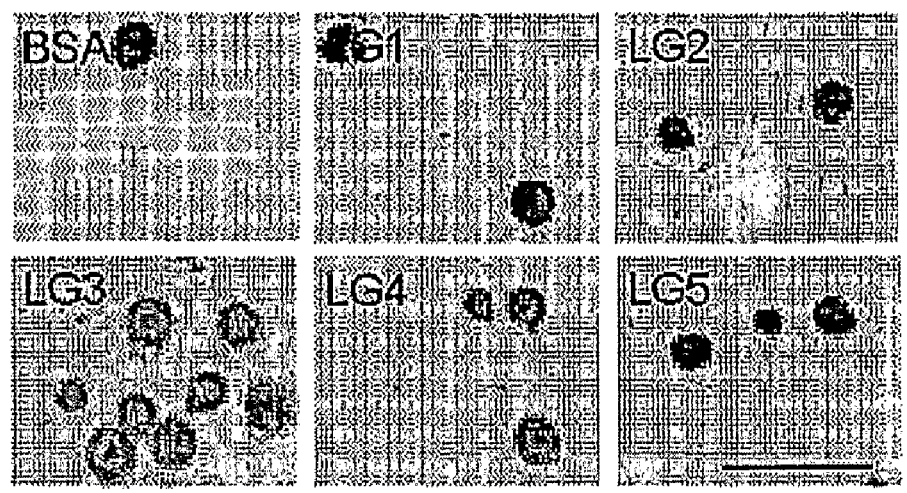
FIG. 2D shows a measurement of cell spreading activities of the recombinant LG proteins in HOK-16B cells.
Figure 2D:
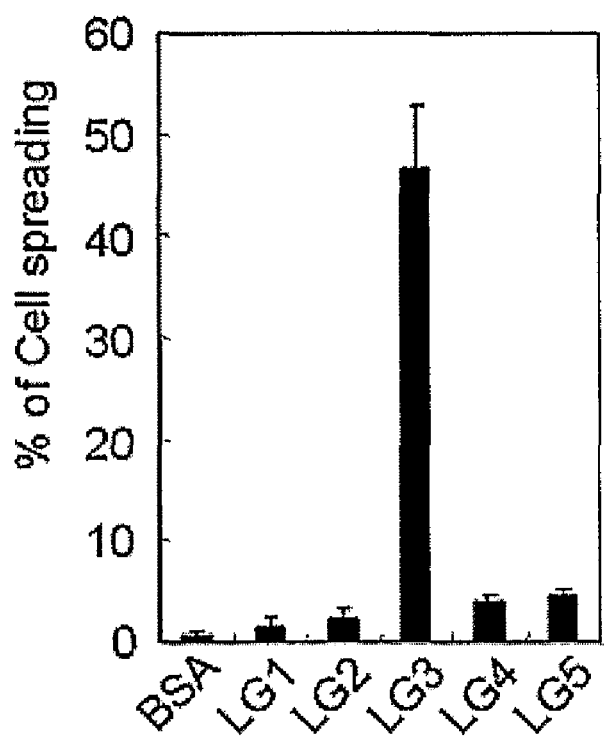

As a result, only rLG3 protein exhibited the adhesive activity among the five rLG proteins (FIGS. 2A-2C). The HOK-16B cell adhesion on rLG3 protein was dose-dependent, with the maximum adhesion occurring at a 25-µg/ml coating concentration (FIG. 2B). In FIG. 2B, BSA and laminin were used as negative and positive controls. At equal or greater coating concentrations, the adhesion activity of rLG1, rLG2, rLG4, and rLG5 proteins displayed marginal adhesion activity compared to the BSA control (FIGS. 2B and 2C). The level of cell adhesion using 50 µg/ml rLG3 protein was found to have approximately 45% reduction compared to the 5 µg/ml laminin-coated control (FIG. 2A)

To further evaluate the adhesion activity of the laminin-5 α3 chain rLG protein, the inventors examined whether the adherent cells were tethered to the substratum or spread over the substratum. In the adhesion assay, the HOK-16B cells attached to the rLG proteins were imaged after washing, fixation, and staining with crystal violet. The adhesion activity profile of the rLG proteins, which was determined by cell counting in the cell adhesion assay, was quite similar to those of the rLG proteins determined by spectrophotometry (FIG. 2C).

As a result of the examination for spreading activity of HOK-16B cells on rLGs by the described method in the Experimental Example 2, 47% of the HOK-16B cells displayed a spreading morphology; that is they adopted a flattened, polygonal shape, with filopodia- and lamellipodia-like extensions (FIG. 2D). The remaining non-spreading cells on the rLG3 protein resisted being washed and remained tethered to the plate surface. In contrast to rLG3, minimal cell spreading was observed on rLG1-, rLG2-, rLG4-, or rLG5-coated plates. These results suggest that the recombinant LG3 domain displays functional properties similar to laminin-5, its parent molecule, because it supports cell adhesion and spreading.

Example 3

Identification of Human Laminin-5 α3 Chain LG Sequence Active for Cell Adhesion and Spreading It is identified that human laminin-5 .alpha.3 chain rLG3 domain mediates cell adhesion and spreading in the Example 2. In addition, the C-terminal 28 amino acids (residues 1297-1324) and 83 amino acids (residues 1214-1296) within the LG3 domain were previously demonstrated to support cell adhesion and cell motility, respectively (Kariya, Y. et al., J. Cell Biochem., 88:506, 2003). Therefore, to identify the essential amino acid residues conferring cell adhesion activity of the laminin .alpha.3 chain LG domain, five overlapping 12-mer peptides covering amino acid residues 1293-1332 derived from the LG3 domain were synthesized by Fmoc (9-fluorenylmethoxycarbonyl)-based solid-phase method using C-terminal amide as Pinoeer peptide synthesizer (Applied Biosystem, Forster City, Calif.) in the Korea Basic Science Institute (FIG. 3). The arrows indicate the locations of the synthetic peptides in the FIG. 3. The predicted 13-strand structures are boxed in gray, and the basic amino acids Lys and Arg of the peptide P4 are boxed in white (hypertext transfer protocol world wide web address: bmm.icnet.uk/.about.3djigsaw/dom_fish). The synthesized peptides were purified by reverse-phase high performance liquid chromatography. Their characteristics were analyzed by high performance liquid chromatography and mass spectrophotometry. Among the synthesized peptides, P1 contains 1293-1304 residues of the amino acid sequence of SEQ ID NO: 2, P2 contains the amino acid sequence corresponding to 1297-1308 residues, P3 contains the amino acid sequence corresponding to 1305-1316 residues, P4 contains the amino sequence corresponding to 1312-1323 residues, and P5 contains the amino sequence corresponding to 1321-1332 residues.

The cell adhesion and spreading activities on peptide-coated plates were examined using HOK-16B cells by the same method as Experimental Example 2. 24-well plates were coated with 10, 20, 30, 40 and 50 µg/well peptides P1 to P5, respectively. HOK-16B cells were added to peptide-coated plates and cultured for 1 h in serum-free medium for 1 hr. After the unbound cells were washed off, adherent cells were fixed and stained with crystal violet, and then the stained cells were analyzed. Absorbance was measured at 570 nm in a microplate reader. BSA and the rLG3 were used as negative control and positive control, respectively.

As a result, peptide P4(PPFLMLLKGSTR), SEQ ID NO: 1, showed a strong dose-dependent cell adhesion activity. The maximum cell adhesion was obtained when peptide P4 was coated on the plates at concentrations ≧10 µg/well. However, peptides P1, P2, and P3 showed no adhesion activity, even at high coating concentrations, while peptide P5 showed a very weak dose-dependent adhesion activity at concentrations ≧25 µg/well (FIG. 4A)

In addition, the adhesion activity profile of peptides at 10 µg/well coating concentration, which was determined by cell counting in the cell adhesion assay, was the same in all peptides except for peptide 4 (FIG. 4B). The cell adhesion activity of peptide P4 was similar to that of the rLG3.

To examine the adhesion activity of peptide P4 in detail, the inventors examined whether the adherent cells were tethered to the substratum or spread over the substratum. The BSA and rLG3 were used as the negative control and positive control, respectively, the percentage of cells displaying a spreading morphology was quantified by dividing the number of spreading cells by the total number of bound cells. As a result, on peptide P4, 35% of the HOK-16B cells displayed a spreading morphology, however, the other peptides showed no spreading (FIG. 4C).

It is recognized that the cell spreading activity of peptide P4 was similar to that of the rLG3 protein. Accordingly, the inventors examined the ability of peptide P4 to compete for cell adhesion activity to rLG3 domain by the method of Experimental Example 4. First, the purified rLG3 proteins (25 µg/well) were coated onto 24-well plates. HOK-16B cells were preincubated with the various peptides (100 µg/ml) or without the peptide for 30 min at 37° C. The preincubated cells were then added to rLG3-coated plates and cultured for 1 h in serum-free medium. The unbound cells were washed off and the adherent cells were fixed and stained with crystal violet. The average adhesion activity of the control cultures (HOK-16B cells preincubated without peptide) was considered 100%, the results are expressed as mean ±SD of the four independent experiments. Thus, the synthetic peptide P4 inhibited cell adhesion to rLG3 by approximately 51%, but none of the other peptides showed reduced adhesion activity in HOK-16B cells preincubated for 30 min with 100 µg/ml of the peptides. Overall, these results suggest that the peptide P4 sequence (PPFLMLLKGSTR),SEQ ID NO: 1, functions as a cell binding site in the intact laminin-5 α3 chain LG3 domain.

Example 4

Cell Adhesion to rLG3 Protein and Peptide P4 is Dependent on Integrin α3β1

Figure 5A:
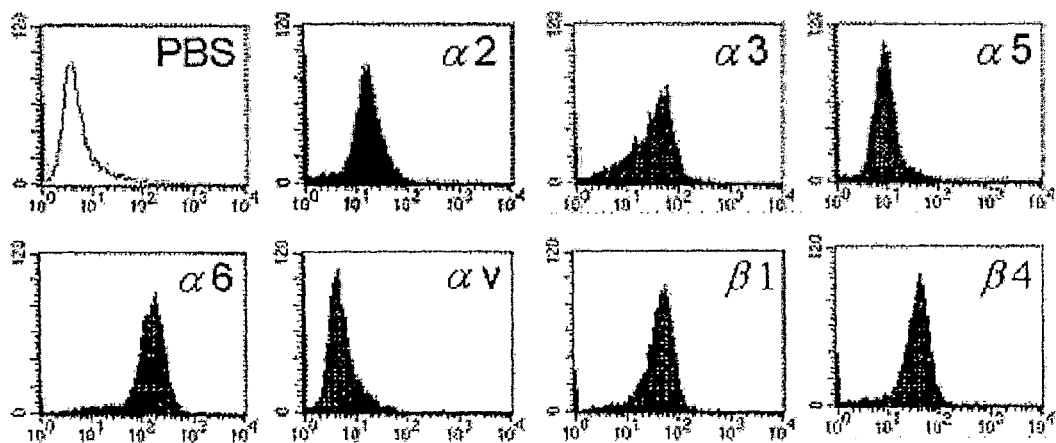
FIG. 5A shows results of flow cytometry of integrin subunits on HOK-16B cells.

To identify a cell surface receptor participating in cell adhesion and spreading activities of recombinant LG3 domain and peptide P4, the present inventors determined the kinds of integerins expressed on the surface of the HOK-16B cells by FACS using function-blocking monoclonal mAbs (Chemicon Temecula, Calif.) against integrin subunits. As in Experimental Example 3, HOK-16B cells were cultured with mABs specific to α2, α3, α5, α6, αv, β1 or β4 integrin subunits, to perform flow cytometry by staining with FITC-conjugation secondary antibodies. At this time, the negative controls were cultured with secondary antibodies only. The result was showed as function of fluorescence intensity (x coordinate) by the number of plotted cells (y coordinate). As a result, it is confirmed that the HOK-16B cells expressed several integrins, including α3β1, α6β1, and α6β4 (FIG. 5A).

Figure 5B:
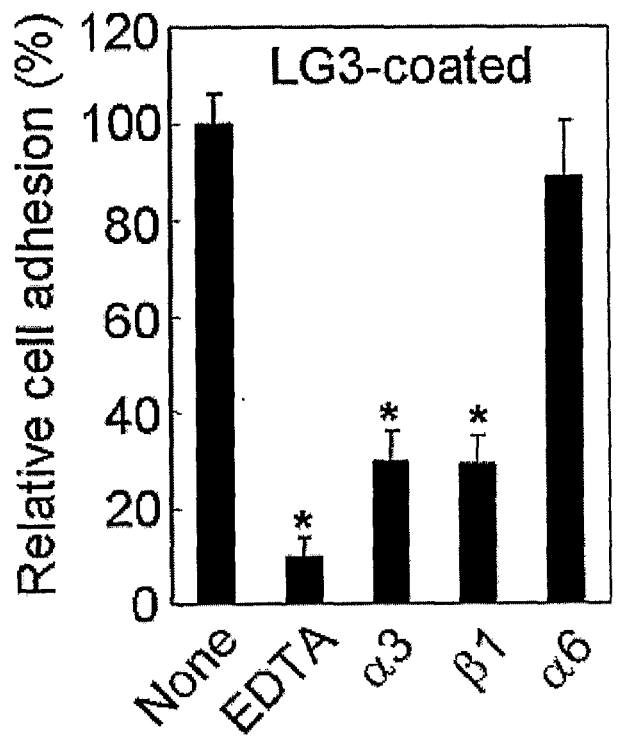
FIG. 5B shows inhibition of cell adhesion activity of recombinant LG3 proteins in human laminin-5 α3 chain by antibodies to the integrin α3β1.

Meanwhile, the ligand-integrin interaction were known to require a divalent cation. To determine the role of cations in the interaction, the present inventors examined the effect of metal-chelating reagent, EDTA, on HOK-16B cell adhesion to the rLG3- and peptide P4-coated plates. HOK-16B cells were preincubated with 5 mM EDTA or 5 µg/ml function-blocking mAbs (Chemicon Temecula, CA) against integrin α3 (P1B5), β1 (6S6), α6 (NK I-GoH3) subunits for 30 min at 37° C. and plated on 25 µg/ml rLG3-precoated plate, and then cultured for 1 hr. After the unbound cells were washed off, the adherent cells were fixed to stain with crystal violet, and the stained cells were analyzed. The average adhesion activity of control cultures (HOK-16B cells preincubated without EDTA or integrin antibodies) were considered 100%. As a result, cell adhesion to rLG3 was almost completely inhibited by 5 mM EDTA (FIG. 5B). Similarly, a decrease in cell adhesion was observed on 10 µg/well of peptide P4-coated plates in the presence of 5 mM EDTA, even if the inhibitory effect of EDTA was lower than that on rLG3 protein. This suggests that the cell surface receptor for rLG3 protein and peptide P4 might be one of the integrins that require divalent cations for their interaction with the ligands.

Figure 5C:
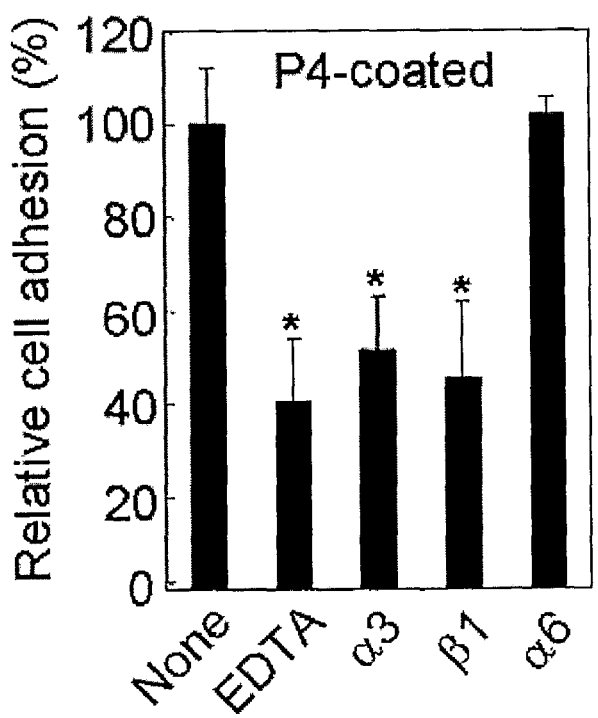
FIG. 5C shows inhibition of cell adhesion activity of synthetic peptide P4 derived from human laminin-5 α3 chain LG3 domain by antibodies to the integrin α3β1.

Also, the inventors examined the effect of function-blocking mAbs to integrin subunits on the adhesion activity of HOK-16B cells to a surface coated with rLG3 protein or peptide P4. As a result, adhesion to the rLG3 protein- or peptide P4-coated surface was specifically inhibited by antibodies to the α3 and β1 subunits (FIGS. 5B and 5C). Treatment of HOK-16B cells with the anti-integrin α3 antibody inhibited the cell adhesion activities of rLG3 and peptide P4 by 71% and 49%, respectively, whereas treatment with anti-integrin β1 antibody inhibited the cell adhesion activities of rLG3 and peptide P4 by 71% and 54% %, respectively. From the results, it is suggested that integrin α3β1 is a specific functional receptor for both rLG3 and peptide P4 in HOK-16B cells and that the cell adhesion activity of peptide P4 toward the HOK-16B cells is mediated by a slightly weak interaction with integrin α3β1 compared to the rLG3 protein.

Example 5

Cell Adhesion Activity of C-Terminal Truncated and Ala-Substituted Peptides of Peptide P4

It was observed that peptide P4 promotes strong cell adhesion and spreading activities and binds to integrin α3β1 in the Example 4. Therefore, to determine the biologically active core sequences in peptide P4, five synthetic peptides (P4 D-I to P4 D-V), which are C-terminal truncated peptides from the peptide P4, and six synthetic peptides (P4 D-N1 to P4 D-N6), which are N-terminal truncated peptides from the peptide P4 were prepared (FIG. 6A) and examined for HOK-16B cell adhesion and spreading activities on peptide-coated plates by the present inventors. 24-well plates were coated with 10 µg/well C-terminal truncated peptides or N-terminal truncated peptides, and HOK-16B cells were added to the plates, and then cultured in serum-free medium for 1 hr. After the unbound cells were washed off, the adherent cells were fixed to stain with crystal violet, and the stained cells were analyzed. Absorbance was measured at 570 nm in a microplate reader. Peptide P4 and BSA were used as the positive and negative controls, respectively.

As a result, peptide P4 D-I, which has a deletion of the C-terminal Arg residue in peptide P4, showed a significantly lower cell adhesion activity than the peptide P4 control (FIGS. 6B and 6C). However, further deletion of the C-terminal amino acid residues in peptide P4 showed similar or slightly decreased cell adhesion activity than that of P4 D-I. Likewise, the cell spreading activity using the five C-terminal truncated peptides was also significantly lower than the peptide P4 control (FIG. 6D), and cell spreading morphology was almost the same as cell adhesion profile.

It was observed that a deletion of the C-terminal Arg residue in peptide P4 significantly reduced the cell adhesion activity.

Also, peptide P4 D-N1, which has a deletion of one residue of two N-terminal Pro residues in peptide P4, did not show a significantly lower cell adhesion and spreading activities than the peptide P4 control, whereas, peptide P4 D-N2, which has a deletion of two N-terminal Pro residues in peptide P4, showed a significantly lower cell adhesion and spreading activities than the peptide P4 control (FIGS. 6C and 6D). However, further deletion of the N-terminal amino acid residues in peptide P4 showed similar or significantly decreased cell adhesion and spreading activities compared to P4 having a deletion of C-terminal amino acid.

To verify the role of two basic amino acid residues, Arg and Lys, in the peptide P4 sequence for cell adhesion activity, the present inventors prepared synthetic peptides (P4-S1 to P4-S3) by substituting Ala for both/each basic amino acids $Lys^{1319}$ and $Arg^{1323}$ in peptide P4 (FIG. 7A), and examined their cell adhesion and spreading activities on peptide-coated plates using HOK-16B cells (FIGS. 7B and 7C).

24-well plates were coated with 10 µg/well peptides, and HOK-16B cells were added to the plates, and then cultured in serum-free medium for 1 hr. After the unbound cells were washed off, the adherent cells were fixed to stain with crystal violet, and the stained cells were analyzed. Peptide P4 and BSA were used as the positive and negative controls, respectively. The results were expressed as mean ±SD of the four independent experiments.

As a result, the cell adhesion and spreading were significantly inhibited by peptides P4-S2, in which Ala substituted for Arg, and P4-S3, in which Ala substituted for both Lys and Arg, compared to the peptide P4 control. However, these activities were unaffected by peptide P4-S1 where Ala substituted for only Lys (FIGS. 7B and 7C). From these results, the basic residue Arg is essential for cell adhesion and spreading activities of peptide P4. These results suggest that the PPFLMLLKGSTR (SEQ ID NO: 1) sequence (1312-1323 residues) within the laminin-5α3 chain LG3 domain is an active motif responsible for cell adhesion and spreading and for integrin α3β1 binding.

Example 6

Effect of rLG3- or Peptide P4 on FAK Phosphorylation at Tyr-397 and -577

It was demonstrated that integrins function not only as adhesion receptors, but also as signal transducers (Schwartz, M. A. et al., Ann. Rev. Cell. Dev. Biol., 11:549, 1995; Shoenwaelder, S. M. and Burridge, K., J. Biol. Chem., 274:14359, 1999). The activation of integrins upon cell adhesion to the exreacellular matrix protein leads to an increase in phosphorylation of the FAK (focal adhesion kinase), which is the major tyrosine phosphorylated protein following cell adhesion to the components of the extracellular matrix protein (Clark, E. A. and Brugge, J. S., Science, 268:233, 1995; Guan, J. L., *Int. J. Biochem. Cell Biol.,* 29:1085, 1997; Giancotti, F. G. and Ruoslahti, E., *Science,* 285:1028, 1999). It was identified that FAK Tyr-397, -407, -576, -577, -861, and -925 were phospho-acceptor sites. Among them, the Tyr-397 was reported to be a major site in FAK auto-phosphorylation (Schlaepfer, D. D. et al., *Nature,* 372:786, 1994).

To examine the signaling pathways mediated by either the LG3 domain or peptide P4, the phosphorylation of FAK was examined in HOK-16B cells plated on either rLG3 or peptide P4. Laminin was included as the control ligand binding to the α3β1 integrin (Lampe, P. D. et al., *J. Cell Biol.,* 143:1735, 1998). First, the FAK phosphorylation levels at Tyr-397 on laminin-coated and uncoated plates were alnaylzed using HOK-16B cells for 15, 30, or 60 min by the method described in Experimental Example 5.

HOK-16B cells isolated by trypsinization were suspended for 1 hr, and kept in suspension (Sus), or replated on 60-mm culture dishes coated with or without laminin (5 µg/ml). The cells were kept for 15, 30, or 60 min for being attached on plates, then cell lysates were analyzed by immunoblot analysis with anti-FAK p-Y397 antibody (Biosource, Camariollo, Calif.). As a result, the extent of FAK phosphorylation in HOK-16B cells on laminin was notably higher than that in HOK-16B cells which were either plated on plastic or kept in suspension. This effect was observed within 15 min and peaked at 15 min after exposure to the laminin-coated plate (FIG. 8A).

Therefore, the extent of FAK phosphorylation at Tyr-397,-407,-576, -577, and -861 was investigated in HOK-16B cells cultured on plates coated with laminin (5 µg/ml), rLG3 (25 µg/ml), or peptides P1-P5 (50 µg/60-mm dish) for 15 min. The lysates were immnoblotted with polyclonal anti-FAK, p-Y397, p-Y407, p-Y576, p-Y577 or p-Y861 antibodies (Biosoucce, Camariollo, Calif.), and the total FAK level was detected using anti-FAK antibodies (Upstate Biotechnology, Lake Placid, N.Y. The ratio of p-FAK to t-FAK (p-FAK/t-FAK) for each sample was then calculated to correct for differences in protein loading. This ratio was normalized to the p-FAK/t-FAK ratio of the negative controls (cells on plates) to obtain the relative fold induction of FAK phosphorylation. As a result, the extent of FAK phosphorylation at Tyr-397 cultured on the laminin-coated or rLG3 protein-coated plates increased 16.2- and 8.2-fold compared with the untreated control (FIG. 8B). These results prove that laminin induces FAK phosphorylation at Tyr (Clark, E. A. and Brugge, J. S., *Science,* 268:233, 1995; Guan, J. L., *Int. J. Biochem. Cell Biol.,* 29:1085, 1997; Giancotti, F. G. and Ruoslahti, E., *Science,* 285:1028, 1999).

Figure 8C:
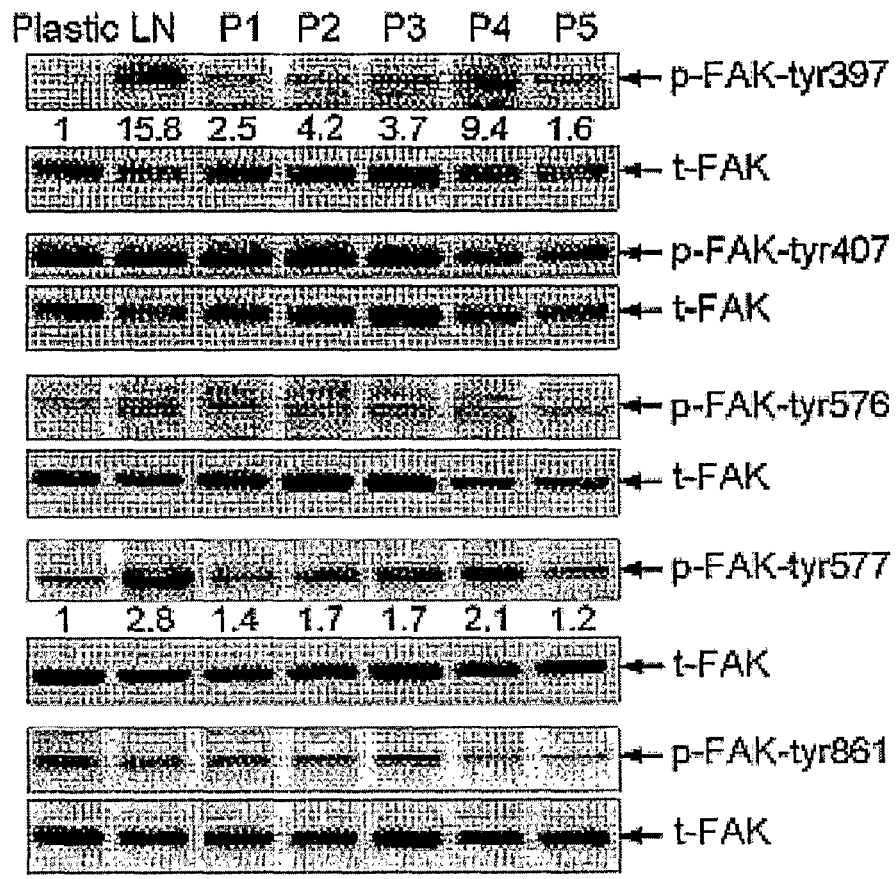
FIG. 8C shows the effect of synthetic peptides derived from human laminin-5 α3 LG3 domain on FAK phosphorylation at various tyrosine sites by immunoblot analysis.

Although the FAK phosphorylation level of Tyr-397 in cells adhering to peptide P4 was lower than that of laminin, the levels were much higher on peptide P4, which induced cell adhesion, than on other peptides (FIG. 8C). In addition, the level of FAK phosphorylation at Tyr-577 in the cells plated on peptide P4 was higher than that in the cells spread on the other peptides, but was lower than that on laminin. However, these changes of the FAK phosphorylation levels at Tyr-407, -576 and -861 were not observed in laminin, rLG3 and other peptides under similar condition. This suggest that laminin, rLG3, and peptide P4 activate the distinct integrin α3β1-mediated signaling pathways.

Figure 8D:
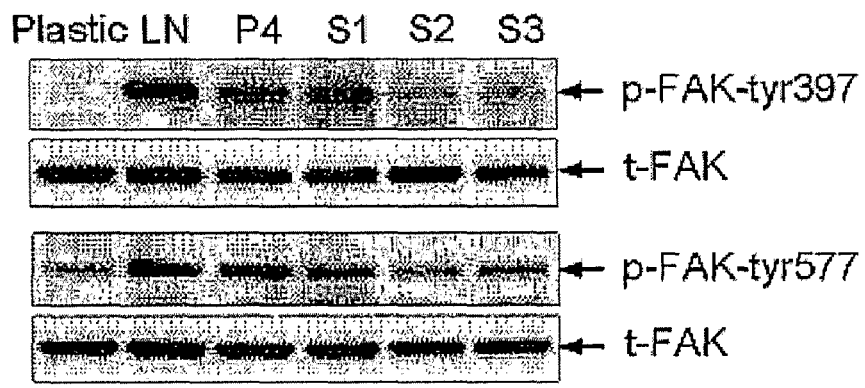
FIG. 8D shows the effect of Ala-substituted peptides (P4-S1-P4 S3) of peptide P4 on FAK phosphorylation at tyrosine -397, -577 by immunoblot analysis.

Since peptides P4-S2 having Ala substituted for Arg, and P4-S3 having Ala substituted for both Arg and Lys, significantly inhibit cell adhesion compared with the peptide P4 control, the present inventors investigated that the levels of FAK phosphorylation at Tyr-397 and -577 in HOK-16B cells adhering to peptides P4-S1 to P4-S3 to verify the role of the two basic amino acid residues in the peptide P4 sequence on Tyr phosphorylation of FAK. The FAK phosphorylation level of Tyr-397 in cells plated on peptide P4-S1 having Ala substituted for Lys was similar to that on peptide P4. In contrast, the FAK phosphorylation levels in the cells plated on peptides P4-S2 and P4-S3 were significantly decreased compared with the peptide P4 control (upper panel of FIG. 8D). Such changes at FAK Tyr-577 were also observed on peptides P4-S1 to P4-S3 under similar conditions (lower panel of FIG. 8D). These results suggest that the basic residue Arg$^{1323}$ in peptide P4, which is tightly correlated to the level of cell adhesion, is required for Tyr phoshphorylation of FAK.

Example 7

Measurement of Cell Adhesion Activities of NHEK and NHEF by P4 Peptide 7-1: NHEK Preparation Normal human epidermal keratinocytes (NHEK) tissue samples were prepared from foreskin tissue of healthy 1- to 3-year-old people. The tissue samples were washed three times with calcium- and magnesium-free Hanks balanced salt solution containing 3× antibiotics (CMF-HBSS; GibcoBRL), and added with CMF-HBSS containing collgenase (collgenase type II, 1.0 mg/ml; sigma Chemical Co.) and dispase (dispase grade II, 2.4 mg/ml; Boeringer-Mannheim) to isolate epithelial layer from epidermal tissue, and then, cultured in 95% air and 5% $CO_2$ at 37° C. for 90 min. NHEKs were prepared from the isolated epidermal tissue, and cultured in epithelial cell medium containing 0.15 mM calcium and growth factor bullet kit (KGM; Clonetics Corp.). When cell density was about 70%, NHEKs were divided into 1×10$^5$ cells per 60-mm petri dish and cultured until cell density reached about 70%. NHEKs were subcultured two times the same way as the above and used.

7-2: NHEF Preparation

Normal human epidermal fibroblasts (NHEF) were taken from foreskin tissue of healthy 1- to 3-year-old people, and washed three times with calcium- and magnesium-free Hanks balanced salt solution containing 3× antibiotics (CMF-HBSS; GibcoBRL), and prepared by explant culture. When cell density was about 80%, NHEFs were divided by the ratio of 1:3 and cultured until cell density reached about 80%. NHEKs were subcultured 4 times the same way as the above and used.

7-3: Identification of Proliferation Promotion of Epithelial Cells and Epidermal Fibroblasts Polystyrene (PS), BSA (bovine serum albumin) and synthetic peptide P4 were coated on 24-well plates. NHEK (PD 13.0; 2×10$^4$ cells/12-well plate) and NHEF (passage number 4) cultures were added to the 12-well plate coated with the polystyrene (PS), BSA (1%) and synthetic peptide P4 (20 µg/12-well plate), and cultured for 1, 2, 3, or 4 days. Viable cells were counted by trypan blue exclusion in a hemocytometer. Data are expressed as mean ±SD (n=4).

With respect to the measurement results, FIGS. 9A and 9B show an increase in the numbers of NHEKs and NHEFs according to cell proliferation, respectively. As illustrated, the number of NHEKs and NHEFs on plates coated with BSA was the fewest, and an increase in the number of cells according to cell proliferation on plates coated with PS and peptide P4 was similar. In case of NHEKs, the number of NHEKs on peptide P4-coated plate increased more than that on PS-coated plate. It is confirmed that peptide P4 was especially useful for NHEK cell proliferation.

7-4: Measurement of Cell Adhesion Activity

Beschitin W microfiber having diameter of 14-mm (UNITIKA Co., Japan) was placed in 24-well culture dish, and 0.4 ml bovine serum albumin (1 mg/ml), control peptide P1 (10 μg/well) or functional peptide (P4, 10 μg/well) were added, and the culture dish was subjected to drying coating for 12 hr at room temperature. In case of testing only Beschitin W microfiber, 0.4 ml phosphate buffered saline (PBS) were added, and the culture dish was subjected to the same treatment. To block the peptide-uncoated site, 0.4 ml/well bovine serum albumin (1 mg/ml) was added, and cultured for 30 min at 37° C. Then, bovine serum albumin was removed, and washed with PBS carefully. $1 \times 10^5$ cells/well (0.5 ml) were spread, and cultured in 95% air and 5% $CO_2$ at 37° C. for 60 min. Epithelial cell culture broth containing 0.15 mM calcium and growth factor bullet kit (KGM; Clonetics Corp.) was used in this step. The culture broth was removed, and the plates were rinsed once with PBS carefully, and then 0.4 ml of 10% formalin in PBS was added. The cells were left to stand for 15 min at room temperature to fix. Fixing solution was removed, and the plates were washed twice with PBS, and then cells attached to Beschitin W microfiber were stained with hematoxylin-eosin solution. Staining solution was removed, and the plates were then rinsed 3 times with DDW carefully, and then the cells attached to Beschitin W microfiber were photographed. To ensure a representative value, Beschitin W microfiber was divided into quarters; two fields per quarter were photographed using an Olympus BX51 microscope at 100× magnification. The average percentage and standard deviation were calculated from four independent experiments. FIGS. 10A to 10C show the photographs and the calculation results of cell adhesion activity and spreading activity.

As illustrated in FIGS. 10A to 10C, when commercially available artificial skin material, Beschitin W microfiber, was coated with peptide P4 of the present invention, excellent cell adhesion activity and spreading activity were shown. From this result, it is confirmed that peptide P4 according to the present invention is useful for wound healing or tissue regeneration.

Example 8

Identification of Cell Adhesion Activity and Spreading Activity of Peptide P4 through Animal Experiments

8-1: Conditions of Animal Experiment

Sprague-Dawley rats weighing 240±10 g were used for this experiment. After anesthetization, two full-thickness rectangular wounds of 1 cm×1 cm parallel with a spinal column were prepared on each back of rats. The peptide P4-coated Beschitin W microfiber were then applied to the wounds of each rat. The same wound was treated with only Beschitin W microfiber as a control. The 3rd or 7th day after treatment, each wound was removed for histological examination of epithelialization and granulation.

8-2: Wound Healing and Histological Examination

Figure 11A:
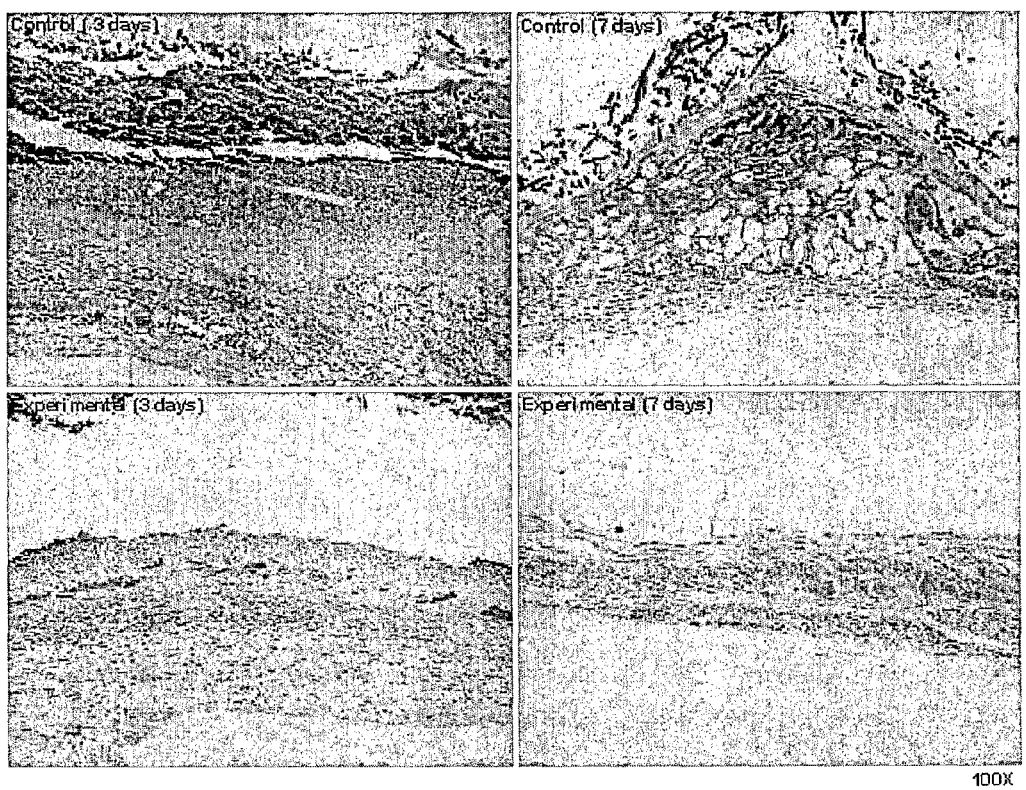
FIG. 11 shows results of animal experiment to identify in vivo function of peptide P4, which are photomicrographs showing process of wound healing of rat skin on the 3rd day and 7th day (FIG. 11A: H&E, 100×.
FIG. 11B: H&E, 200×).
Figure 11B:
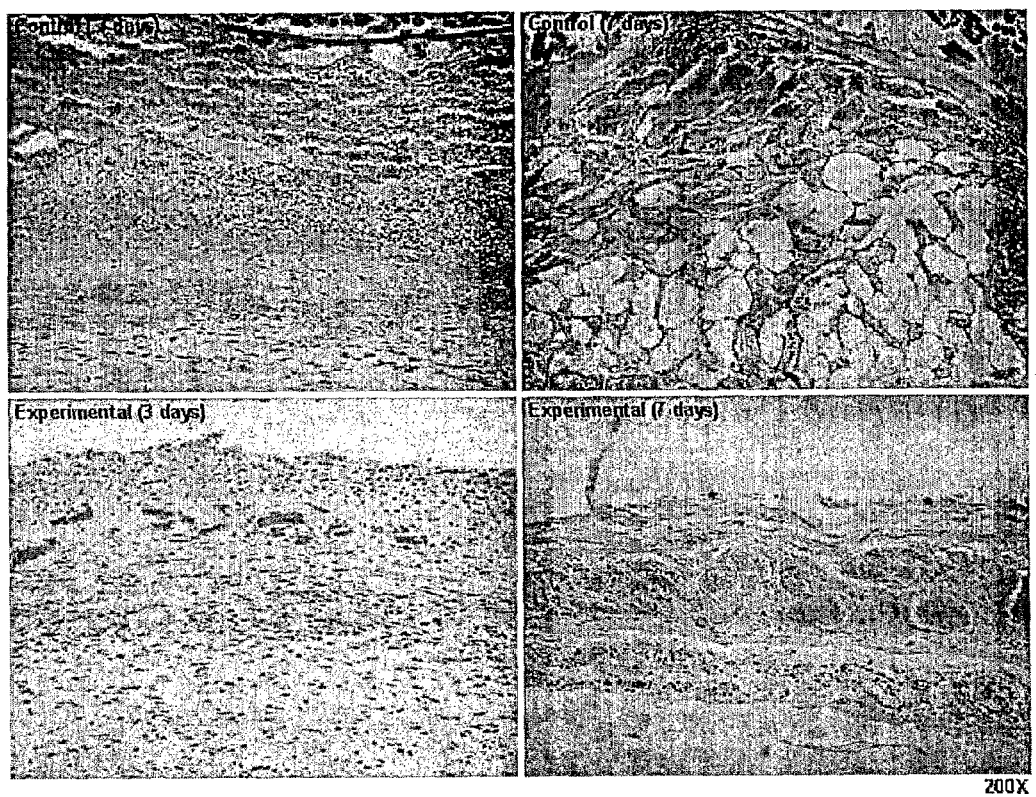

For histological examination, results of peptide P4-coated Beschitin W microfiber groups and control groups of the 3rd and 7th days were examined by microscope. FIGS. 11A and 11B illustrates 100× and 200× photomicrographs, respectively.

In the control groups of the 3rd and 7th days, the wound surface was covered with fibrinous tissue debris, and below that layer, dense infiltration of polymorphonuclear leukocytes and proliferation of fibroblasts were observed. In the 3rd and 7th days of Beschitin W microfiber group coated with peptide P4, however, the surface tissue debris disappeared, and there was remarkable proliferation of young capillaries and fibroblasts.

In both groups, epithelialization of the wound was complete after 4 weeks. Additionally, inflammatory cells disappeared and connective tissue was densely formed. In the 7th day of peptide P4-coated Beshchitin W microfiber group, however, the surface tissue debris disappeared, and there was remarkable proliferation of young capillaries and fibroblasts.

These animal experiment results demonstrated that early-stage healing in the peptide P4-coated Beschitin W microfiber group was faster than that in the control group with only Beschitin W microfiber.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above in detail, the inventive peptide containing amino acid sequence of SEQ ID NO: 1, fragments and derivatives thereof promoted cell adhesion and spreading by binding specifically to integrin α3β1 thus will be useful for research on cell adhesion activity, wound care, tissue regeneration, inhibition of cancer metastasis etc. mediated by various extracellular matrix proteins including laminin.

---

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Pro Pro Phe Leu Met Leu Leu Lys Gly Ser Thr Arg
1               5                   10
```

<210> SEQ ID NO 2
<211> LENGTH: 1713
<212> TYPE: PRT
<213> ORGANISM: Homo sapiens

<400> SEQUENCE: 2

```
Met Gly Trp Leu Trp Ile Phe Gly Ala Ala Leu Gly Gln Cys Leu Gly
1               5                   10                  15

Tyr Ser Ser Gln Gln Gln Arg Val Pro Phe Leu Gln Pro Pro Gly Gln
            20                  25                  30

Ser Gln Leu Gln Ala Ser Tyr Val Glu Phe Arg Pro Ser Gln Gly Cys
        35                  40                  45

Ser Pro Gly Tyr Tyr Arg Asp His Lys Gly Leu Tyr Thr Gly Arg Cys
    50                  55                  60

Val Pro Cys Asn Cys Asn Gly His Ser Asn Gln Cys Gln Asp Gly Ser
65                  70                  75                  80

Gly Ile Cys Val Asn Cys Gln His Asn Thr Ala Gly Glu His Cys Glu
                85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
    210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                245                 250                 255

Tyr Arg Ser Ala Ile Ser Asn His Gly Ser Lys Ile Glu Gly Leu Glu
            260                 265                 270

Arg Glu Leu Thr Asp Leu Asn Gln Glu Phe Glu Thr Leu Gln Glu Lys
        275                 280                 285

Ala Gln Val Asn Ser Arg Lys Ala Gln Thr Leu Asn Asn Asn Val Asn
    290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                325                 330                 335

Glu Gly Asn Asn Val Pro Ser Gly Asp Phe Ser Arg Glu Trp Ala Glu
            340                 345                 350

Ala Gln Arg Met Met Arg Glu Leu Arg Asn Arg Asn Phe Gly Lys His
        355                 360                 365

Leu Arg Glu Ala Glu Ala Asp Lys Arg Glu Ser Gln Leu Leu Leu Asn
    370                 375                 380
```

```
Arg Ile Arg Thr Trp Gln Lys Thr His Gln Gly Glu Asn Asn Gly Leu
385                 390                 395                 400

Ala Asn Ser Ile Arg Asp Ser Leu Asn Glu Tyr Glu Ala Lys Leu Ser
            405                 410                 415

Asp Leu Arg Ala Arg Leu Gln Glu Ala Ala Gln Ala Lys Gln Ala
        420                 425                 430

Asn Gly Leu Asn Gln Glu Asn Glu Arg Ala Leu Gly Ala Ile Gln Arg
            435                 440                 445

Gln Val Lys Glu Ile Asn Ser Leu Gln Ser Asp Phe Thr Lys Tyr Leu
        450                 455                 460

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
            485                 490                 495

Glu Ala Arg Gln Glu Leu Ser Asp Lys Val Arg Glu Leu Ser Arg Ser
            500                 505                 510

Ala Gly Lys Thr Ser Leu Val Glu Glu Ala Glu Lys His Ala Arg Ser
        515                 520                 525

Leu Gln Glu Leu Ala Lys Gln Leu Glu Glu Ile Lys Arg Asn Ala Ser
530                 535                 540

Gly Asp Glu Leu Val Arg Cys Ala Val Asp Ala Thr Ala Tyr Glu
545                 550                 555                 560

Asn Ile Leu Asn Ala Ile Lys Ala Ala Glu Asp Ala Ala Asn Arg Ala
            565                 570                 575

Ala Ser Ala Ser Glu Ser Ala Leu Gln Thr Val Ile Lys Glu Asp Leu
        580                 585                 590

Pro Arg Lys Ala Lys Thr Leu Ser Ser Asn Ser Asp Lys Leu Leu Asn
        595                 600                 605

Glu Ala Lys Met Thr Gln Lys Lys Leu Lys Gln Glu Val Ser Pro Ala
        610                 615                 620

Leu Asn Asn Leu Gln Gln Thr Leu Asn Ile Val Thr Val Gln Lys Glu
625                 630                 635                 640

Val Ile Asp Thr Asn Leu Thr Thr Leu Arg Asp Gly Leu His Gly Ile
            645                 650                 655

Gln Arg Gly Asp Ile Asp Ala Met Ile Ser Ser Ala Lys Ser Met Val
        660                 665                 670

Arg Lys Ala Asn Asp Ile Thr Asp Glu Val Leu Asp Gly Leu Asn Pro
        675                 680                 685

Ile Gln Thr Asp Val Glu Arg Ile Lys Asp Thr Tyr Gly Arg Thr Gln
        690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
            725                 730                 735

Asn Gln Gln Leu Leu Pro Leu Gly Asn Ile Ser Asp Asn Met Asp Arg
            740                 745                 750

Ile Arg Glu Leu Ile Gln Gln Ala Arg Asp Ala Ala Ser Lys Val Ala
        755                 760                 765

Val Pro Met Arg Phe Asn Gly Lys Ser Gly Val Glu Val Arg Leu Pro
        770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
```

-continued

```
                805                 810                 815
Met Tyr Leu Gly Asn Lys Asp Ala Ser Arg Asp Tyr Ile Gly Met Ala
            820                 825                 830

Val Val Asp Gly Gln Leu Thr Cys Val Tyr Asn Leu Gly Asp Arg Glu
            835                 840                 845

Ala Glu Leu Gln Val Asp Gln Ile Leu Thr Lys Ser Glu Thr Lys Glu
            850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
            885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
            915                 920                 925

Leu Pro Ser Arg Leu Ser Phe Pro Pro Tyr Lys Gly Cys Ile Glu Leu
            930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
            965                 970                 975

Glu Ser Asp Lys Asn Tyr Phe Glu Gly Thr Gly Tyr Ala Arg Val Pro
            980                 985                 990

Thr Gln Pro His Ala Pro Ile Pro Thr Phe Gly Gln Thr Ile Gln Thr
            995                 1000                1005

Thr Val Asp Arg Gly Leu Leu Phe Phe Ala Glu Asn Gly Asp Arg
            1010                1015                1020

Phe Ile Ser Leu Asn Ile Glu Asp Gly Lys Leu Met Val Arg Tyr
            1025                1030                1035

Lys Leu Asn Ser Glu Leu Pro Lys Glu Arg Gly Val Gly Asp Ala
            1040                1045                1050

Ile Asn Asn Gly Arg Asp His Ser Ile Gln Ile Lys Ile Gly Lys
            1055                1060                1065

Leu Gln Lys Arg Met Trp Ile Asn Val Asp Val Gln Asn Thr Ile
            1070                1075                1080

Ile Asp Gly Glu Val Phe Asp Phe Ser Thr Tyr Tyr Leu Gly Gly
            1085                1090                1095

Ile Pro Ile Ala Ile Arg Glu Arg Phe Asn Ile Ser Thr Pro Ala
            1100                1105                1110

Phe Arg Gly Cys Met Lys Asn Leu Lys Lys Thr Ser Gly Val Val
            1115                1120                1125

Arg Leu Asn Asp Thr Val Gly Val Thr Lys Lys Cys Ser Glu Asp
            1130                1135                1140

Trp Lys Leu Val Arg Ser Ala Ser Phe Ser Arg Gly Gly Gln Leu
            1145                1150                1155

Ser Phe Thr Asp Leu Gly Leu Pro Pro Thr Asp His Leu Gln Ala
            1160                1165                1170

Ser Phe Gly Phe Gln Thr Phe Gln Pro Ser Gly Ile Leu Leu Asp
            1175                1180                1185

His Gln Thr Trp Thr Arg Asn Leu Gln Val Thr Leu Glu Asp Gly
            1190                1195                1200

Tyr Ile Glu Leu Ser Thr Ser Asp Ser Gly Gly Pro Ile Phe Lys
            1205                1210                1215
```

```
Ser Pro Gln Thr Tyr Met Asp Gly Leu Leu His Tyr Val Ser Val
    1220            1225                1230
Ile Ser Asp Asn Ser Gly Leu Arg Leu Leu Ile Asp Asp Gln Leu
    1235            1240                1245
Leu Arg Asn Ser Lys Arg Leu Lys His Ile Ser Ser Ser Arg Gln
    1250            1255                1260
Ser Leu Arg Leu Gly Gly Ser Asn Phe Glu Gly Cys Ile Ser Asn
    1265            1270                1275
Val Phe Val Gln Arg Leu Ser Leu Ser Pro Glu Val Leu Asp Leu
    1280            1285                1290
Thr Ser Asn Ser Leu Lys Arg Asp Val Ser Leu Gly Gly Cys Ser
    1295            1300                1305
Leu Asn Lys Pro Pro Phe Leu Met Leu Leu Lys Gly Ser Thr Arg
    1310            1315                1320
Phe Asn Lys Thr Lys Thr Phe Arg Ile Asn Gln Leu Leu Gln Asp
    1325            1330                1335
Thr Pro Val Ala Ser Pro Arg Ser Val Lys Val Trp Gln Asp Ala
    1340            1345                1350
Cys Ser Pro Leu Pro Lys Thr Gln Ala Asn His Gly Ala Leu Gln
    1355            1360                1365
Phe Gly Asp Ile Pro Thr Ser His Leu Leu Phe Lys Leu Pro Gln
    1370            1375                1380
Glu Leu Leu Lys Pro Arg Ser Gln Phe Ala Val Asp Met Gln Thr
    1385            1390                1395
Thr Ser Ser Arg Gly Leu Val Phe His Thr Gly Thr Lys Asn Ser
    1400            1405                1410
Phe Met Ala Leu Tyr Leu Ser Lys Gly Arg Leu Val Phe Ala Leu
    1415            1420                1425
Gly Thr Asp Gly Lys Lys Leu Arg Ile Lys Ser Lys Glu Lys Cys
    1430            1435                1440
Asn Asp Gly Lys Trp His Thr Val Val Phe Gly His Asp Gly Glu
    1445            1450                1455
Lys Gly Arg Leu Val Val Asp Gly Leu Arg Ala Arg Glu Gly Ser
    1460            1465                1470
Leu Pro Gly Asn Ser Thr Ile Ser Ile Arg Ala Pro Val Tyr Leu
    1475            1480                1485
Gly Ser Pro Pro Ser Gly Lys Pro Lys Ser Leu Pro Thr Asn Ser
    1490            1495                1500
Phe Val Gly Cys Leu Lys Asn Phe Gln Leu Asp Ser Lys Pro Leu
    1505            1510                1515
Tyr Thr Pro Ser Ser Ser Phe Gly Val Ser Ser Cys Leu Gly Gly
    1520            1525                1530
Pro Leu Glu Lys Gly Ile Tyr Phe Ser Glu Glu Gly Gly His Val
    1535            1540                1545
Val Leu Ala His Ser Val Leu Leu Gly Pro Glu Phe Lys Leu Val
    1550            1555                1560
Phe Ser Ile Arg Pro Arg Ser Leu Thr Gly Ile Leu Ile His Ile
    1565            1570                1575
Gly Ser Gln Pro Gly Lys His Leu Cys Val Tyr Leu Glu Ala Gly
    1580            1585                1590
Lys Val Thr Ala Ser Met Asp Ser Gly Ala Gly Gly Thr Ser Thr
    1595            1600                1605
```

-continued

| | | | | | | | | | | | |
|---|---|---|---|---|---|---|---|---|---|---|---|
| Ser | Val<br>1610 | Thr | Pro | Lys | Ser<br>1615 | Leu | Cys | Asp | Gly<br>1620 | Gln | Trp His Ser |
| Val | Ala<br>1625 | Val | Thr | Ile | Lys<br>1630 | Gln | His | Ile | Leu<br>1635 | His | Leu Glu Leu Asp |
| Thr | Asp<br>1640 | Ser | Ser | Tyr | Thr<br>1645 | Ala | Gly | Gln | Ile<br>1650 | Pro | Phe Pro Pro Ala |
| Ser | Thr<br>1655 | Gln | Glu | Pro | Leu<br>1660 | His | Leu | Gly | Gly<br>1665 | Ala | Pro Ala Asn Leu |
| Thr | Thr<br>1670 | Leu | Arg | Ile | Pro<br>1675 | Val | Trp | Lys | Ser<br>1680 | Phe | Phe Gly Cys Leu |
| Arg | Asn<br>1685 | Ile | His | Val | Asn<br>1690 | His | Ile | Pro | Val<br>1695 | Pro | Val Thr Glu Ala |
| Leu | Glu<br>1700 | Val | Gln | Gly | Pro<br>1705 | Val | Ser | Leu | Asn<br>1710 | Gly | Cys Pro Asp Gln |

<210> SEQ ID NO 3
<211> LENGTH: 18
<212> TYPE: DNA
<213> ORGANISM: Artificial Sequence
<220> FEATURE:
<223> OTHER INFORMATION: Synthetic Construct

<400> SEQUENCE: 3
tccgactgcc aaatgacc                                                                          18

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
ctgactcttc cttcctcctt ctac                                                                   24

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
aaaaacattc aatctcaaca caac                                                                   24

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gatcgcacaa gcttccagtc t                                                                      21

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7

-continued

```
tcgttagatt gaatgatact gtgg                                          24
```

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8

```
catgattggc ctgggtctt                                                19
```

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9

```
agatgcttgc tcaccacttc c                                             21
```

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10

```
caatacagag tgagccaaga cgac                                          24
```

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11

```
ttcttcaagc ttcggggtgt c                                             21
```

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12

```
tgctgtgaaa taggcttggg ttac                                          24
```

<210> SEQ ID NO 13
<211> LENGTH: 311
<212> TYPE: PRT
<213> ORGANISM: Artificial Sequence
<220> FEATURE:
<223> OTHER INFORMATION: Synthetic Construct

<400> SEQUENCE: 13

```
Met Arg Gly Ser His His His His His His Gly Met Ala Ser Met Thr
1               5                  10                  15

Gly Gly Gln Gln Met Gly Arg Asp Leu Thr Asp Asp Asp Lys Asp
            20                  25                  30

Pro Ser Arg Ser Ala Ala Gly Thr Met Glu Phe Asp Phe Val Arg
```

-continued

```
                35                  40                  45
Leu Asn Asp Thr Val Gly Val Thr Lys Lys Cys Ser Glu Asp Trp Lys
    50                  55                  60
Leu Val Arg Ser Ala Ser Phe Ser Arg Gly Gly Gln Leu Ser Phe Thr
65                  70                  75                  80
Asp Leu Gly Leu Pro Pro Thr Asp His Leu Gln Ala Ser Phe Gly Phe
                85                                      95
Gln Thr Phe Gln Pro Ser Gly Ile Leu Leu Asp His Gln Thr Trp Thr
                100                 105                 110
Arg Asn Leu Gln Val Thr Leu Glu Asp Gly Tyr Ile Glu Leu Ser Thr
                115                 120                 125
Ser Asp Ser Gly Gly Pro Ile Phe Lys Ser Pro Gln Thr Tyr Met Asp
    130                 135                 140
Gly Leu Leu His Tyr Val Ser Val Ile Ser Asp Asn Ser Gly Leu Arg
145                 150                 155                 160
Leu Leu Ile Asp Asp Gln Leu Leu Arg Asn Ser Lys Arg Leu Lys His
                165                 170                 175
Ile Ser Ser Ser Arg Gln Ser Leu Arg Leu Gly Gly Ser Asn Phe Glu
                180                 185                 190
Gly Cys Ile Ser Asn Val Phe Val Gln Arg Leu Ser Leu Ser Pro Glu
                195                 200                 205
Val Leu Asp Leu Thr Ser Asn Ser Leu Lys Arg Asp Val Ser Leu Gly
    210                 215                 220
Gly Cys Ser Leu Asn Lys Pro Pro Phe Leu Met Leu Leu Lys Gly Ser
225                 230                 235                 240
Thr Arg Phe Asn Lys Thr Lys Thr Phe Arg Ile Asn Gln Leu Leu Gln
                245                 250                 255
Asp Thr Pro Val Ala Ser Pro Arg Ser Val Lys Val Trp Gln Asp Ala
                260                 265                 270
Cys Ser Pro Leu Pro Lys Thr Gln Ala Asn His Glu Ser Leu Val Asn
                275                 280                 285
Ser Leu Leu Asp Pro Ala Ala Asn Lys Ala Arg Lys Val Ala Glu Leu
    290                 295                 300
Ala Ala Ala Thr Ala Glu Gln
305                 310
```

What is claimed is:

1. A peptide for promoting cell adhesion and spreading, wherein the peptide is selected from the group consisting of (a) a peptide consisting of SEQ ID NO: 1, (b) a fragment of SEQ ID NO: 1, wherein the fragment is selected from the group consisting of SEQ ID NO: 18, SEQ ID NO: 19, SEQ ID NO: 20, SEQ ID NO: 21, SEQ ID NO: 22, SEQ ID NO: 23 and SEQ ID NO: 24 and (c) a derivative of SEQ ID NO: 1, wherein the derivative is selected from the group consisting of SEQ ID NO: 29, SEQ ID NO: 30 and SEQ ID NO: 31.

2. The peptide according to claim 1, wherein Arg at amino acid position 12 in SEQ ID NO: 1 is conserved.

3. The peptide according to claim 1, wherein Pro at amino acid position 1 or 2 in SEQ ID NO: 1 is conserved.

4. The peptide according to claim 1, wherein the peptide mediates cell adhesion and spreading through integrin α3β1.

5. A composition comprising a peptide, wherein the peptide is selected from the group consisting of (a) a peptide consisting of SEQ ID NO: 1, (b) a fragment of SEQ ID NO: 1, wherein the fragment is selected from the group consisting of SEQ ID NO: 18, SEQ ID NO: 19, SEQ ID NO: 20, SEQ ID NO: 21, SEQ ID NO: 22, SEQ ID NO: 23 and SEQ ID NO: 24 and (c) a derivative of SEQ ID NO: 1, wherein the derivative is selected from the group consisting of SEQ ID NO: 29, SEQ ID NO: 30 and SEQ ID NO: 31.

6. A wound covering material comprising the peptide of claim 1.

7. A scaffold for tissue engineering comprising the peptide of claim 1.

* * * * *

UNITED STATES PATENT AND TRADEMARK OFFICE
CERTIFICATE OF CORRECTION

PATENT NO. : 7,517,654 B2
APPLICATION NO. : 10/555590
DATED : April 14, 2009
INVENTOR(S) : Byung-Moo Min It is certified that error appears in the above-identified patent and that said Letters Patent is hereby corrected as shown below:

Column 12, line 17: "I/III" should be -- I/II --.

Column 33, line 53, insert:

--
<210> SEQ ID NO 14
<211> LENGTH: 40
<212> TYPE: PRT
<213> ORGANISM: Artificial Sequence
<220> FEATURE
<223> OTHER INFORMATION: part of the laminin alpha LG3 domain of Humans

<400> SEQUENCE: 14

Leu Thr Ser Asn Ser Leu Lys Arg Asp Val Ser Leu Gly Gly Cys Ser
1               5                   10                  15
Leu Asn Lys Pro Pro Phe Leu Met Leu Leu Lys Gly Ser Thr Arg Phe
            20                  25                  30
Asn Lys Thr Lys Thr Phe Arg Ile
        35                  40

<210> SEQ ID NO 15
<211> LENGTH: 40
<212> TYPE: PRT
<213> ORGANISM: Artificial Sequence
<220> FEATURE
<223> OTHER INFORMATION: part of the laminin alpha LG3 domain of rats

<400> SEQUENCE: 15

Leu Ala Ser Lys Ser Thr Lys Lys Asp Ala Ser Leu Gly Gly Cys Ser
1               5                   10                  15
Leu Asn Lys Pro Pro Phe Leu Met Leu Phe Lys Ser Pro Lys Arg Phe
            20                  25                  30
Asn Lys Gly Arg Ile Phe Asn Val
        35                  40

UNITED STATES PATENT AND TRADEMARK OFFICE
CERTIFICATE OF CORRECTION

PATENT NO.        : 7,517,654 B2
APPLICATION NO.   : 10/555590
DATED             : April 14, 2009
INVENTOR(S)       : Byung-Moo Min It is certified that error appears in the above-identified patent and that said Letters Patent is hereby corrected as shown below:

```
<210> SEQ ID NO 16
<211> LENGTH: 40
<212> TYPE: PRT
<213> ORGANISM: Artificial Sequence
<220> FEATURE
<223> OTHER INFORMATION: part of the laminin alpha LG3 domain of mice

<400> SEQUENCE: 16

Met Ala Ser Lys Ser Thr Lys Arg Asp Ala Phe Leu Gly Gly Cys Ser
 1               5                  10                  15
Leu Asn Lys Pro Pro Phe Leu Met Leu Phe Lys Ser Pro Lys Gly Phe
            20                  25                  30
Asn Lys Ala Arg Ser Phe Asn Val
            35                  40

<210> SEQ ID NO 17
<211> LENGTH: 40
<212> TYPE: PRT
<213> ORGANISM: Artificial Sequence
<220> FEATURE
<223> OTHER INFORMATION: part of the laminin alpha LG3 domain of dogs

<400> SEQUENCE: 17

Leu Ala Ser Lys Thr Phe Lys Arg Asp Val Ser Leu Gly Gly Cys Ser
 1               5                  10                  15
Leu Asn Lys Pro Pro Phe Leu Met Leu Leu Arg Gly Ser Thr Arg Leu
            20                  25                  30
Asn Lys Ser His Thr Phe Asn Ile
            35                  40
```

UNITED STATES PATENT AND TRADEMARK OFFICE
CERTIFICATE OF CORRECTION

PATENT NO.         : 7,517,654 B2
APPLICATION NO.    : 10/555590
DATED              : April 14, 2009
INVENTOR(S)        : Byung-Moo Min It is certified that error appears in the above-identified patent and that said Letters Patent is hereby corrected as shown below:

```
<210> SEQ ID NO 18
<211> LENGTH: 11
<212> TYPE: PRT
<213> ORGANISM: Artificial Sequence
<220> FEATURE
<223> OTHER INFORMATION: peptide P4 D-I

<400> SEQUENCE: 18

Pro Pro Phe Leu Met Leu Leu Lys Gly Ser Thr
1               5                   10

<210> SEQ ID NO 19
<211> LENGTH: 10
<212> TYPE: PRT
<213> ORGANISM: Artificial Sequence
<220> FEATURE
<223> OTHER INFORMATION: peptide P4 D-II

<400> SEQUENCE: 19

Pro Pro Phe Leu Met Leu Leu Lys Gly Ser
1               5                   10

<210> SEQ ID NO 20
<211> LENGTH: 9
<212> TYPE: PRT
<213> ORGANISM: Artificial Sequence
<220> FEATURE
<223> OTHER INFORMATION: peptide P4 D-III

<400> SEQUENCE: 20

Pro Pro Phe Leu Met Leu Leu Lys Gly
1               5
```

UNITED STATES PATENT AND TRADEMARK OFFICE
CERTIFICATE OF CORRECTION

PATENT NO.         : 7,517,654 B2                                     Page 4 of 7
APPLICATION NO.    : 10/555590
DATED              : April 14, 2009
INVENTOR(S)        : Byung-Moo Min It is certified that error appears in the above-identified patent and that said Letters Patent is hereby corrected as shown below:

```
<210> SEQ ID NO 21
<211> LENGTH: 8
<212> TYPE: PRT
<213> ORGANISM: Artificial Sequence
<220> FEATURE
<223> OTHER INFORMATION: peptide P4 D-IV

<400> SEQUENCE: 21

Pro Pro Phe Leu Met Leu Leu Lys
1               5

<210> SEQ ID NO 22
<211> LENGTH: 7
<212> TYPE: PRT
<213> ORGANISM: Artificial Sequence
<220> FEATURE
<223> OTHER INFORMATION: peptide P4 D-V

<400> SEQUENCE: 22

Pro Pro Phe Leu Met Leu Leu
1               5

<210> SEQ ID NO 23
<211> LENGTH: 11
<212> TYPE: PRT
<213> ORGANISM: Artificial Sequence
<220> FEATURE
<223> OTHER INFORMATION: peptide P4 D-N1

<400> SEQUENCE: 23

Pro Phe Leu Met Leu Leu Lys Gly Ser Thr Arg
1               5                   10
```

UNITED STATES PATENT AND TRADEMARK OFFICE
CERTIFICATE OF CORRECTION

PATENT NO. : 7,517,654 B2
APPLICATION NO. : 10/555590
DATED : April 14, 2009
INVENTOR(S) : Byung-Moo Min It is certified that error appears in the above-identified patent and that said Letters Patent is hereby corrected as shown below:

```
<210> SEQ ID NO 24
<211> LENGTH: 10
<212> TYPE: PRT
<213> ORGANISM: Artificial Sequence
<220> FEATURE
<223> OTHER INFORMATION: peptide P4 D-N2

<400> SEQUENCE: 24

Phe Leu Met Leu Leu Lys Gly Ser Thr Arg
1               5                   10

<210> SEQ ID NO 25
<211> LENGTH: 9
<212> TYPE: PRT
<213> ORGANISM: Artificial Sequence
<220> FEATURE
<223> OTHER INFORMATION: peptide P4 D-N3

<400> SEQUENCE: 25

Leu Met Leu Leu Lys Gly Ser Thr Arg
1               5

<210> SEQ ID NO 26
<211> LENGTH: 8
<212> TYPE: PRT
<213> ORGANISM: Artificial Sequence
<220> FEATURE
<223> OTHER INFORMATION: peptide P4 D-N4

<400> SEQUENCE: 26

Met Leu Leu Lys Gly Ser Thr Arg
1               5
```

UNITED STATES PATENT AND TRADEMARK OFFICE
CERTIFICATE OF CORRECTION

PATENT NO.      : 7,517,654 B2
APPLICATION NO. : 10/555590
DATED           : April 14, 2009
INVENTOR(S)     : Byung-Moo Min It is certified that error appears in the above-identified patent and that said Letters Patent is hereby corrected as shown below:

```
<210> SEQ ID NO 27
<211> LENGTH: 7
<212> TYPE: PRT
<213> ORGANISM: Artificial Sequence
<220> FEATURE
<223> OTHER INFORMATION: peptide P4 D-N5

<400> SEQUENCE: 27

Leu Leu Lys Gly Ser Thr Arg
1               5

<210> SEQ ID NO 28
<211> LENGTH: 6
<212> TYPE: PRT
<213> ORGANISM: Artificial Sequence
<220> FEATURE
<223> OTHER INFORMATION: peptide P4 D-N6

<400> SEQUENCE: 28

Leu Lys Gly Ser Thr Arg
1               5

<210> SEQ ID NO 29
<211> LENGTH: 12
<212> TYPE: PRT
<213> ORGANISM: Artificial Sequence
<220> FEATURE
<223> OTHER INFORMATION: peptide P4-S1

<400> SEQUENCE: 29

Pro Pro Phe Leu Met Leu Leu Ala Gly Ser Thr Arg
1               5                   10
```

UNITED STATES PATENT AND TRADEMARK OFFICE
CERTIFICATE OF CORRECTION

PATENT NO.       : 7,517,654 B2
APPLICATION NO.  : 10/555590
DATED            : April 14, 2009
INVENTOR(S)      : Byung-Moo Min It is certified that error appears in the above-identified patent and that said Letters Patent is hereby corrected as shown below:

```
<210> SEQ ID NO 30
<211> LENGTH: 12
<212> TYPE: PRT
<213> ORGANISM: Artificial Sequence
<220> FEATURE
<223> OTHER INFORMATION: peptide P4-S2

<400> SEQUENCE: 30

Pro Pro Phe Leu Met Leu Leu Lys Gly Ser Thr Ala
1               5                   10

<210> SEQ ID NO 31
<211> LENGTH: 12
<212> TYPE: PRT
<213> ORGANISM: Artificial Sequence
<220> FEATURE
<223> OTHER INFORMATION: peptide P4-S3

<400> SEQUENCE: 31

Pro Pro Phe Leu Met Leu Leu Ala Gly Ser Thr Ala
1               5                   10
```

Signed and Sealed this

Twenty-first Day of July, 2009

JOHN DOLL
*Acting Director of the United States Patent and Trademark Office*